(12) United States Patent
Hall et al.

(10) Patent No.: US 6,581,438 B1
(45) Date of Patent: Jun. 24, 2003

(54) CAPILLARY TEST SPECIMEN, SYSTEM, AND METHODS FOR IN-SITU VISUALIZATION OF CAPILLARY FLOW AND FILLET FORMATION

(75) Inventors: Aaron C. Hall, Albuquerque, NM (US); F. Michael Hosking, Albuquerque, NM (US); Mark Reece, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 10/146,095

(22) Filed: May 15, 2002

Related U.S. Application Data

(60) Provisional application No. 60/353,382, filed on Jan. 31, 2002.

(51) Int. Cl.[7] .............................................. G01N 11/00
(52) U.S. Cl. ...................................................... 73/53.01
(58) Field of Search ........................... 73/53.01, 53.04; 356/375, 376

(56) References Cited

U.S. PATENT DOCUMENTS

| | | | | |
|---|---|---|---|---|
| 5,192,983 A | * | 3/1993 | Tokura | 356/376 |
| 5,611,149 A | * | 3/1997 | Fujiwara | 33/833 |
| 5,792,941 A | | 8/1998 | Rye et al. | 73/53.01 |
| 5,827,951 A | | 10/1998 | Yost et al. | |
| 5,910,844 A | * | 6/1999 | Phillips | 356/375 |
| 6,286,368 B1 | | 9/2001 | Solomon et al. | 73/437 |

OTHER PUBLICATIONS

Childree, Patent Application US 20020041822A1, Apr. 11, 2002.*

Hosking et al., "Visual Observations of Liquid Filler Metal Flow Through a Braze Gap", Jan. 22, 2002, Abstract, Sandia National Laboratores, from www.aws.org/conferences/contents.htm.*

Lugschieder and Iversen, "*Investigations on the Capillary Flow of Brazing Filler Metal BN15*", Oct. 1977, pp. 319–324.

Ichiro, Yoshiharu, Yasuhiro, Shun' Ichi & Hisaaki, "*A Development of In–Process Image Processing Technique for Measuring the Molten Area of Braze Filler Metal in Torch Brazing*", Mar. 7, 2002 pp. 1212–1215.

Cohen, Castle and Waldron, "*High–temperature Observations of Braze Alloy Spreading by Oxide Penetration*", Vo. 15 Oct. 1981, pp. 455–462.

* cited by examiner

*Primary Examiner*—Helen Kwok
*Assistant Examiner*—Charles Garber
(74) *Attorney, Agent, or Firm*—Robert D. Watson

(57) ABSTRACT

A capillary test specimen, method, and system for visualizing and quantifying capillary flow of liquids under realistic conditions, including polymer underfilling, injection molding, soldering, brazing, and casting. The capillary test specimen simulates complex joint geometries and has an open cross-section to permit easy visual access from the side. A high-speed, high-magnification camera system records the location and shape of the moving liquid front in real-time, in-situ as it flows out of a source cavity, through an open capillary channel between two surfaces having a controlled capillary gap, and into an open fillet cavity, where it subsequently forms a fillet on free surfaces that have been configured to simulate realistic joint geometries. Electric resistance heating rapidly heats the test specimen, without using a furnace. Image-processing software analyzes the recorded images and calculates the velocity of the moving liquid front, fillet contact angles, and shape of the fillet's meniscus, among other parameters.

21 Claims, 18 Drawing Sheets

Sec. B-B

Sec. B-B

CAPILLARY TEST SPECIMEN, SYSTEM, AND METHODS FOR IN-SITU VISUALIZATION OF CAPILLARY FLOW AND FILLET FORMATION

CROSS REFERENCE TO RELATED APPLICATIONS

This application claims the benefit of U.S. Provisional Application, "Technique for Visualization of Capillary Flow in a Gap as Applied to Brazing, by A.C. Hall, et al., filed Jan. 31, 2002, Ser. No. 60/353,382, which is herein incorporated by reference.

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

The present invention relates generally to test specimens and methods for evaluating the behavior of a liquid flowing in a capillary channel driven by capillary forces. In particular, the present invention relates to a capillary test specimen, method, and system for in-situ visualizing and quantifying the flow of liquid polymers or molten solders or braze alloys or similar filer materials in capillary channels and gaps, including the formation of fillets at two free surfaces that have been configured to represent realistic joint geometries.

Many industrial processes rely on having predictable and reliable flow of liquids inside capillary channels and gaps, including proper formation of fillets at free surfaces. These processes include low temperature operations (e.g., polymer underfilling of surface-mounted microelectronic packages, polymer encapsulation, polymer injection casting or transfer molding, and secondary oil recovery), as well as high temperature operations (e.g., soldering, brazing, and casting of liquid metals). Brazing has been defined as a group of joining processes that produces coalescence of materials by heating them to a suitable temperature and by using a filler metal having a liquidus temperature above 450 C and below the solidus temperature of the base materials to be joined, whereby the filler metal is distributed between the closely fitted surfaces of the joint by capillary attraction. Soldering, a similar process to brazing, is defined to occur below 450 C. Brazing differs from welding in that in braze processing the intention is to melt only the braze filler metal and not the base materials. Good wetting of the base materials by the liquid filler metal is required to provide intimate contact between them, and to develop the necessary chemical bond for good joint strength.

A variety of test specimens and method have been used to evaluate the wetting properties of a liquid on a solid surface (e.g., sessile drop test, immersion wetting balance, closed capillary flow in a tube, open capillary flow in an open channel or groove, and capillary flow between two closely-spaced parallel plates).

In a sessile drop test, the liquid droplet assumes an equilibrium shape that is dictated by surface free energy considerations at the liquid-vapor interface, the solid-vapor interface, and the solid-liquid interface. The boundary between wetting and non-wetting conditions is generally taken at a contact angle, $\theta_{contact}$, equal to 90 degrees. For $\theta_{contact} < 90$ degrees, wetting occurs; while $\theta_{contact} > 90$ degrees a represents a non-wetting condition (i.e., the lower the angle, the better the wetting). The sessile drop test, however, provides no information about the dynamic (i.e., time-dependent) flow of liquids through a capillary channel, or about the formation of fillets at free surfaces.

In industrial settings, the wetting performance of molten solder is commonly evaluated using commercially available wetting balances. A typical wetting balance suspends a specimen from a weighing device (such as a micro-balance or load cell), then a crucible containing the molten material is lifted and immerses the bottom portion of the specimen into a molten solder or braze pool to a known depth. By accurately measuring the force applied to the specimen during immersion in the pool, the wetting force and times can be determined. Using analytical expressions, the wetting angle can be calculated. An immersion balance, however, does not provide access for visualizing the flow of solder through a capillary channel, or for visualizing the formation of fillets at free surfaces.

In another test specimen, capillary flow of a liquid between two closely spaced parallel plates can be studied by measuring the change in capacitance between the two plates as the liquid flows from one side to the other. This test is commonly used to evaluate the flow behavior of liquid polymers that are used for underfilling surface-mounted microelectronic devices. This test specimen, however, is not suitable for use with electrically conductive liquids, such as solders and brazes. Also, the geometry of two parallel plates does not simulate the geometry of complex braze joints and the associated fillets that form thereon.

The flow of liquids inside a closed capillary channel, such as a simple tube, provides a simple relationship between the liquid surface tension, the capillary radius, the contact angle, and the bulk liquid viscosity. However, opaque tubes block visual access for observing the moving liquid front. Also, a simple tube does not have the complex geometry representative of realistic joint geometries.

An open capillary test specimen and method has been disclosed by Rye, et al, in U.S. Pat. No. 5,792,941, "Measurement of Surface Tension and Viscosity by Open Capillary Techniques". Here, an open capillary channel is provided, such as a V-shaped groove, on a flat, wettable surface. The test specimen has timing marks adjacent to the V-groove, and a source marker in which liquid to be tested is deposited. The capillary flow of liquid as it passes by the timing marks is recorded by a video camera looking down on the specimen. Image processing software is subsequently used to determine the flow time and velocity of the moving liquid front. This measurement of the flow time and velocity can be analytically related to the ratio of surface tension-to-viscosity for the liquid (knowing the groove depth, the groove angle, and the liquid/solid contact angle). This test specimen, however, does not provide the complex geometry representative of realistic joint geometries.

With the exception of two closely-spaced parallel plates, none of the test specimens described above are suitable for studying two different materials in contact with the molten solder or braze (e.g., as found in a metal-to-ceramic joint, or polymer underfill between printed wiring board material and a silicon die).

The need remains, therefore, for a capillary test specimen that allows easy visual access from an open side to observe a cross-section of a braze or solder joint, which has a geometry that closely simulates a realistic joint geometry. Such a test specimen should allow easy access for a high-speed video or digital camera to observe the liquid in-situ as it melts (e.g., for a solder or braze), flows from a reservoir (i.e., source), through an open capillary channel between two surfaces having a controlled capillary gap, and into an open region where it subsequently forms a fillet on free surfaces, where the geometry of the free surfaces have been configured to accurately simulate realistic joint geometries. Also, such a test specimen should be capable of simulating liquid flow between surfaces made of two different materials, e.g., a metal surface and a ceramic surface. Additionally, a system is needed that can rapidly heat the test specimen through representative temperature cycles without using a furnace, which allows the camera to get close enough to the specimen to accurately capture in real-time (in-situ) the location and shape of the moving liquid front. Image-processing software can then be used to calculate the velocity of the moving liquid front, as well as other parameters of importance, such as fillet contact angles and shape of the fillet's meniscus.

Against this background, the present invention was developed.

BRIEF DESCRIPTION OF THE DRAWINGS

The accompanying drawings, which are incorporated in and form part of the specification, illustrate various examples of the present invention and, together with the detailed description, serve to explain the principles of the invention.

SUMMARY OF THE INVENTION

Figure 1A:
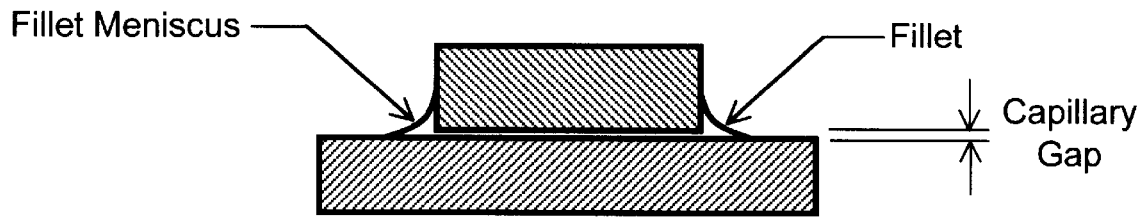
FIG. 1A shows a schematic cross-section view of a common braze joint geometry comprising two flat surfaces butted together, where a fillet has formed between two surfaces oriented at 90 degrees to each other.

The present invention relates to a capillary test specimen, method, and system for visualizing and quantifying capillary flow of liquids under realistic conditions, including polymer underfilling, injection molding, soldering, brazing, and casting. The capillary test specimen simulates complex joint geometries and has an open cross-section between surfaces to permit easy visual access from the side. A high-speed, high-magnification video or digital camera system records the location and shape of the moving liquid front in real-time, in-situ as it flows out of a source cavity, through an open capillary channel between two surfaces having a controlled capillary gap, and into an open fillet cavity, where it subsequently forms a fillet on free surfaces that have been configured to accurately simulate realistic joint fillet geometries. Electric resistance heating or other heat sources rapidly heats the test specimen, without using a furnace. Image-processing software analyzes the recorded images and calculates the velocity of the moving liquid front, fillet contact angles, and shape of the fillet's meniscus, among other parameters.

DETAILED DESCRIPTION OF THE INVENTION

The present invention relates to a capillary test specimen, method, and system for in-situ visualizing and quantifying capillary flow of liquids under realistic conditions, including polymer underfilling, injection molding, soldering, brazing, and casting.

The word "liquid" is broadly defined herein to include conventional materials that are normally liquid at room temperature (e.g., water, oil, drilling fluid, etc.); materials with liquid-like properties (e.g., whose viscosity typically decreases with increasing temperature, such as polymers, polymer/metal particle composites, pastes, slurries, mud, etc.); and materials that are molten (or liquid-like) at elevated temperatures (liquid metals, solders, brazes, glass, etc.). The word "braze" is used interchangeably herein with the word "liquid" as it is defined above. The word "brazing" is broadly defined herein to mean the dynamic flow of any "liquid" (as "liquid" is defined above) between two surfaces that are closely spaced apart by a small capillary gap, where the motion of the liquid is driven by capillary forces. The word "brazing" is also broadly defined herein to mean the dynamic formation of any "liquid" (as "liquid" is defined above) or solidified fillet that forms between two free surfaces, including, but not limited to, polymer underfilling between a surface-mounted microelectronic device package and a substrate, polymer injection/casting, soldering, brazing, and liquid metal casting and infiltration.

The word "braze joint" is broadly defined herein to mean the combination of any two surfaces (i.e., base materials) that are closely-spaced apart by a capillary gap filled with a "liquid" (as "liquid" is defined above. The word "braze joint" is also broadly defined herein to mean the geometrical configuration of a braze joint (as defined above) during the period in which the liquid is flowing, as well as the configuration of a braze joint after liquid flow has stopped, including formation of a stable liquid fillet, and including solidification of previously molten solders, brazes, or other metals.

The phrase "test specimen" is used herein interchangeably with the phrase "capillary test specimen".

The phrase "capillary channel" is defined herein as a geometrical construct comprising the space located in-between at least two solid surfaces that are spaced closely together (i.e., closely-spaced), such that a liquid flows through the channel from one end towards the other driven by the action of capillary forces. The distance (i.e., spacing) between the two solid surfaces is called the capillary gap, and is designated herein as $h_{gap}$. The length of the capillary channel is designated herein as $L_{channel}$. To behave as a capillary channel, the channel's length is generally much greater than the channel's gap, i.e., $L_{channel} >> h_{gap}$ (e.g., greater by a factor of ten or more). In addition, the capillary gap, $h_{gap}$, must be small enough so that capillary forces dominate the overall set of forces acting on the liquid (e.g., gravity). For molten braze or solder alloys, $h_{gap}$ is generally less than about 0.005 inches (but could be larger), and more typically is selected to be from about 0.001 inches to about 0.003 inches. The capillary channel can have a gap smaller than 0.001 inches (e.g., for MEMS or microfluidics devices that are microfabricated by lithographic techniques or micromachining methods). The capillary channel can have a uniform or non-uniform capillary gap along the length of the channel, depending on the application. The capillary channel itself can be straight, curved, or non-straight, depending on the application. The capillary channel can be formed as a groove or channel in a single solid body, or may be defined as the space in-between the facing surfaces of two closely-spaced bodies, as in a braze or solder joint.

The phrase "capillary channel" and "capillary gap" are used interchangeably herein.

The use of the phrase "video camera" is defined herein to include both analog and digital formats and recording mechanisms, unless otherwise specified.

Capillary channels are described herein as being "closed" or "open". A closed capillary channel is one where the flow of liquid by capillary action along the channel cannot be visually observed by a camera or the naked eye (e.g., a long, slender tube made of an opaque material). An open capillary channel is one where the flow of liquid by capillary action along the channel can be visually observed on at least one side of the channel by a camera or the naked eye (e.g., the V-groove capillary channel described in U.S. Pat. No. 5,792, 941, supra, is an open capillary channel). The same definition of "open" applies to a source cavity and to a fillet cavity (i.e., an open source cavity, or an open fillet cavity).

The capillary test specimen of the present invention can easily be modified to represent or simulate a wide range of commonly used braze joint geometries. Some of these commonly used braze joint geometries are illustrated schematically in FIGS. 1A–1F. Other geometries not illustrated are known to one of ordinary skill in the art.

FIG. 1A shows a schematic cross-section view of a common braze joint geometry comprising two flat surfaces butted together, where a fillet has formed between two surfaces oriented at 90 degrees to each other. This is commonly referred to as a "butt joint". If the two surfaces overlap, the joint is commonly referred to as a "lap joint".

Figure 1B:
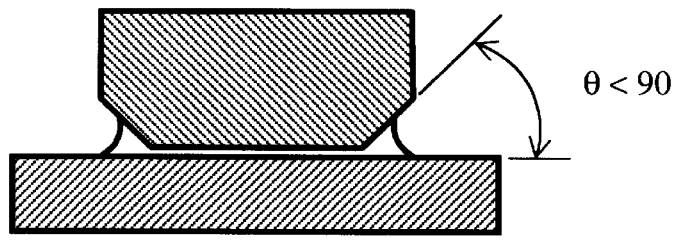
FIG. 1B shows a schematic cross-section view of a common braze joint geometry comprising two flat surfaces butted together, where a fillet has formed between two surfaces oriented at a chamfered angle less than 90 degrees to each other (e.g., at 45 degrees).

FIG. 1B shows a schematic cross-section view of a common braze joint geometry comprising two flat surfaces butted together, where a fillet has formed between two surfaces oriented at a chamfered angle less than 90 degrees to each other (e.g., at 45 degrees).

Figure 1C:
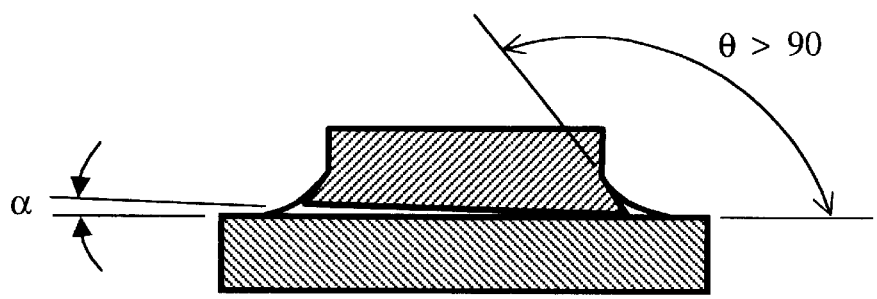
FIG. 1C shows a schematic cross-section view of a common braze joint geometry comprising two flat surfaces butted together, where a fillet has formed between two surfaces oriented at an angle greater than 90 degrees to each other (e.g., at 135 degrees), and where the mating surfaces that butt together are misaligned by a small angle, α.

FIG. 1C shows a schematic cross-section view of a common braze joint geometry comprising two flat surfaces butted together, where a fillet has formed between two surfaces oriented at an angle greater than 90 degrees to each other (e.g., at 135 degrees), and where the mating surfaces that butt together are misaligned by a small angle, α. Misalignment of the two mating surfaces causes the capillary gap to be non-uniform across the braze joint. If both mating surfaces are flat, then the magnitude of the capillary gap, $h_{gap}$, varies linearly as a function of the distance along the capillary channel.

Figure 1D:
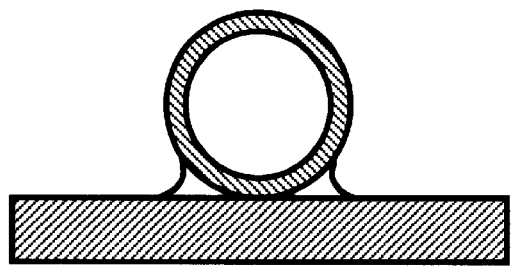
FIG. 1D shows a schematic cross-section view of a common braze joint geometry comprising a tube brazed or soldered to a flat surface.

FIG. 1D shows a schematic cross-section view of a common braze joint geometry comprising a tube brazed or soldered to a flat surface.

Figure 1E:
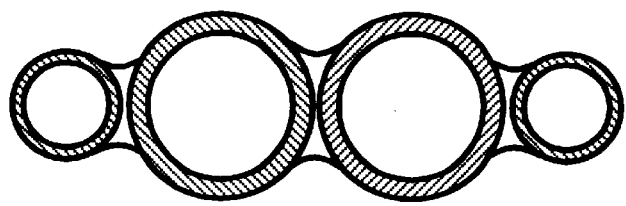
FIG. 1E shows a schematic cross-section view of a common braze joint geometry comprising a bank of tubes joined side-by-side to each other, where some tubes have different diameters than others.

FIG. 1E shows a schematic cross-section view of a common braze joint geometry comprising a bank of tubes joined side-by-side to each other, where some tubes have different diameters than others.

Figure 1F:
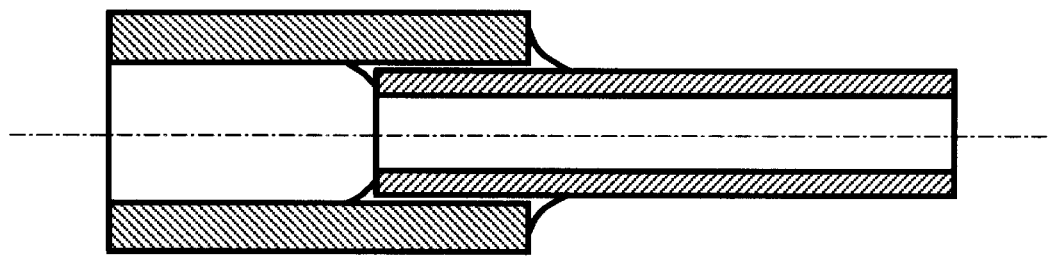
FIG. 1F shows a schematic cross-section view of a common braze joint geometry comprising one tube concentrically located inside of another tube.

FIG. 1F shows a schematic cross-section view of a common braze joint geometry comprising one tube concentrically located inside of another tube. The inner tube is self-centered with respect to the outer tube due to the centering action of capillary forces in the braze joint. This is commonly referred to as a self-centering joint between two concentric bodies.

Figure 2A:
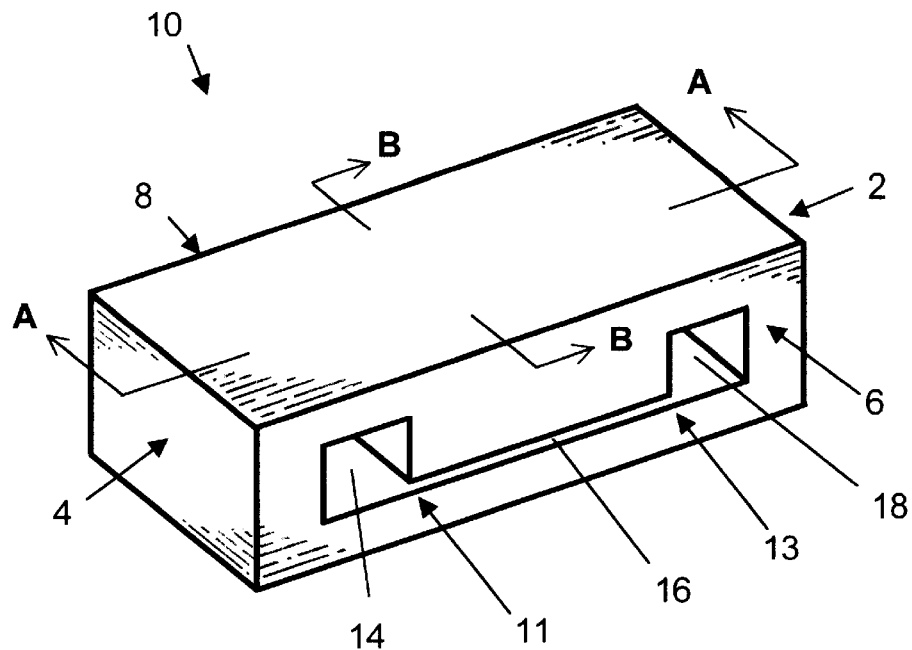
FIG. 2A shows a schematic isometric view of a first example of a capillary test specimen, according to the present invention.

FIG. 2A shows a schematic isometric view of a first example of a capillary test specimen, according to the present invention. Capillary test specimen 10 comprises a solid body 12 with an open capillary channel 16 disposed in body 10. Channel 16 has an entrance 11 and an exit 13. Body 10 further comprises an open source cavity 14, which is fluidically connected to channel 16 at entrance 11. Body 10 further comprises an open fillet cavity 18, which is fluidically connected to channel 16 at exit 13. In this example, body 12 comprises a rectangular parallelepiped having overall dimensions length L, depth D, and height H. The axial length of channel 16 is designated as $L_{channel}$. In this example, source cavity 14, capillary channel 16, and fillet cavity 18 extend completely through body 12, from frontside face 6 through body 12 to backside face 8. In this sense, source cavity 14, capillary channel 16, and fillet cavity 18 are all called "open" because the flow of liquid out of (open) source cavity 14, through (open) capillary channel 16, and into (open) fillet cavity 18 can be easily observed by viewing the outside boundaries of the flowing liquid by looking at the frontside face 6 and/or the backside face 8 of body 12.

It is not required, however, for source cavity 14, fillet cavity 18, and capillary channel 16 to penetrate completely through, body 12 in order to be called "open". All that is needed is for one side of capillary channel 16 and fillet cavity 18 to be easily viewed by a camera or the naked eye. An example of a one-sided configuration will be shown later.

Figure 2B:
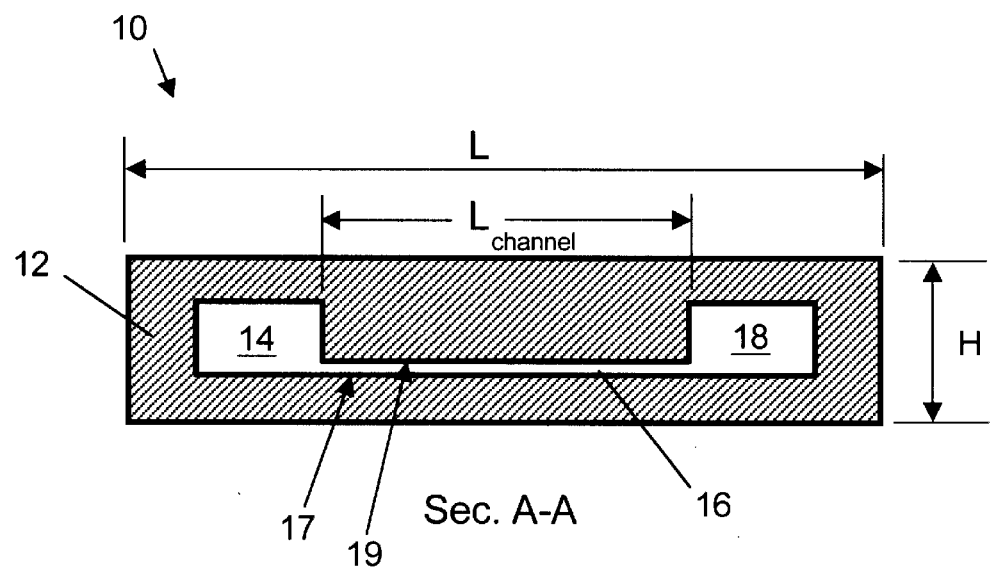
FIG. 2B shows a schematic cross-section view A—A of the example of a capillary test specimen shown in FIG. 2A, according to the present invention.

FIG. 2B shows a schematic cross-section view A—A of the example of a capillary test specimen shown in FIG. 2A, according to the present invention. Source cavity 14 and fillet cavity 18 are both rectangular, and both have approximately the same volume in this example. Capillary channel 16 has two, closely spaced parallel walls 17, 19 separated by a capillary gap, $h_{gap}$. The capillary gap illustrated in these figures has been greatly exaggerated for purposes of illustration only. The volume of source cavity 14 should be greater than the volume of capillary channel 16, so that the source of liquid held in source cavity 14 is sufficient to fill the volume of capillary channel 16 plus at least some of the volume of fillet cavity 18. Test specimen 10 can be fabricated by using a wire electro discharge machine (EDM), laser beam, e-beam, or water-jet to cut out a portion of body 12 that, when removed, leaves an empty volume that defines source cavity 14, fillet cavity 18, and capillary channel 16. When fabricated in this way, test specimen 10 in FIGS. 2A–2C can be described as a single-piece test specimen.

Alternatively, the volume of source cavity 14 can be less than the volume of capillary channel 16, so capillary flow can be studied without fillet formation in fillet cavity 18.

Figure 2C:
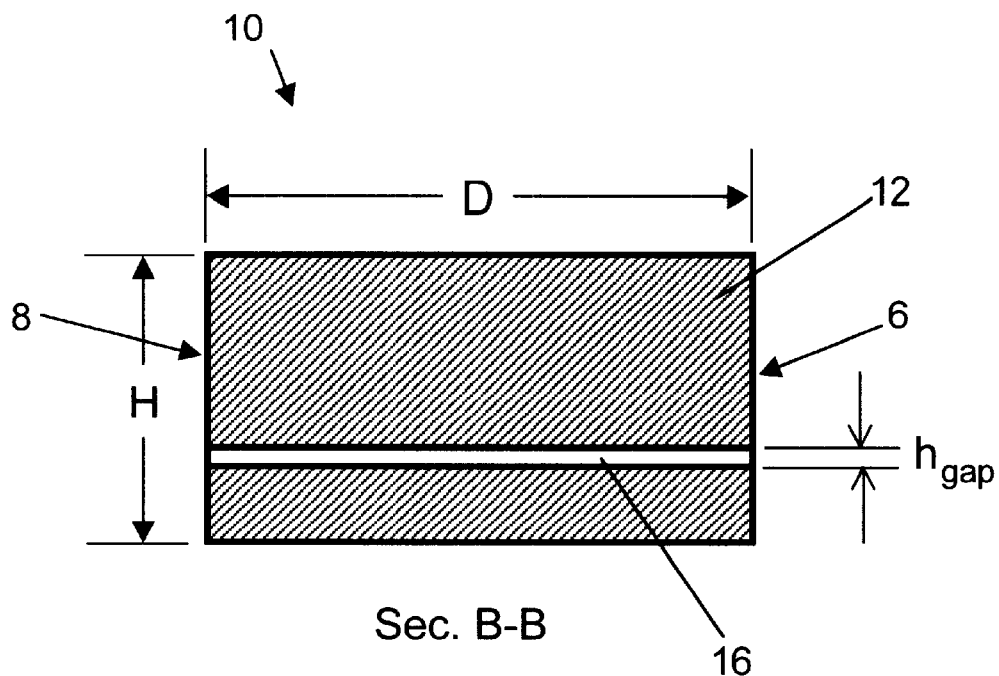
FIG. 2C shows a schematic cross-section view B—B of the example of a capillary test specimen shown in FIG. 2A, according to the present invention.

FIG. 2C shows a schematic cross-section view B—B of the example of a capillary test specimen shown in FIG. 2A, according to the present invention. Capillary channel 16 penetrates completely through body 12 from frontside face 6 to backside face 8. Optionally, the facing surfaces 6 and 8 can be made non-wetting to prevent liquid braze from running out capillary channel 16 and flowing out onto the outside faces. This can be done, for example, by polishing faces 6 and 8 to be very smooth, or by coating faces 6 and 8 with a non-wetting material (e.g., a ceramic-based coating, "stopoff", etc.).

Figure 2D:
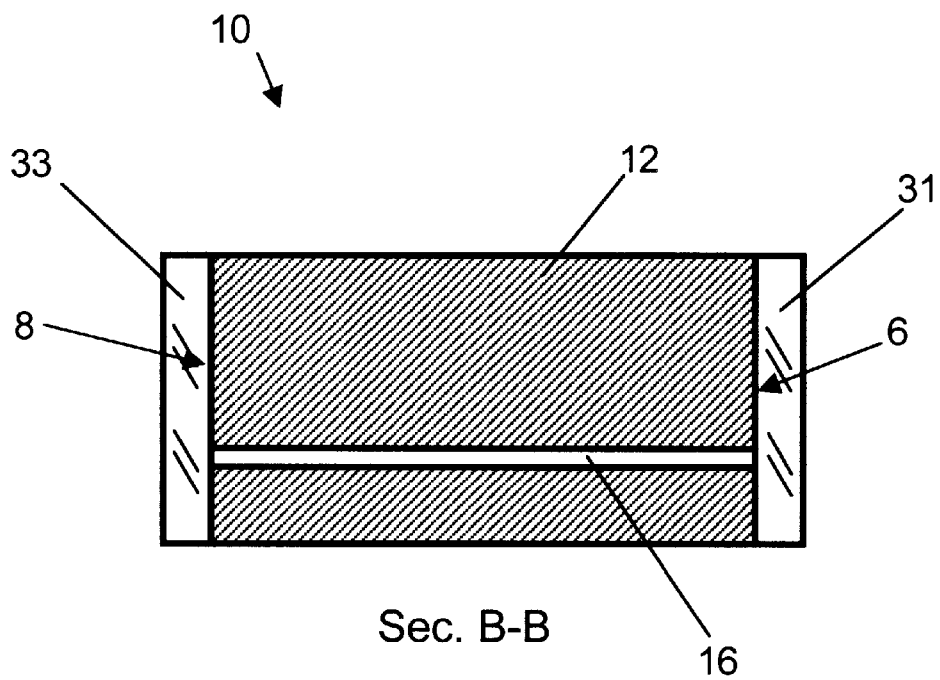
FIG. 2D shows a schematic cross-section view B—B of the example of a capillary test specimen shown in FIG. 2A, with transparent plates on both sides of the specimen, according to the present invention.

FIG. 2D shows a schematic cross-section view B—B of the example of a capillary test specimen shown in FIG. 2A, with transparent plates on both sides of the specimen, according to the present invention. Transparent plates 31 and 33 have been added to sides 6 and 8, respectively, of capillary test specimen 10. Plates 31 and 33 can be made of clear plastic, glass, silica, quartz, or sapphire, depending on the temperature requirements. Optionally, plates 31 and 33 can be made of an IR transparent material, such as silicon. Plates 31 and 33 provide a "closed" physical surface boundary condition for source cavity 14, capillary channel 16, and fillet cavity 18, such that any liquid cannot seep out from inside. However, since plates 31 and 33 are transparent, then source cavity 14, capillary channel 16, and fillet cavity 18, can be considered to effectively be "open", since the flow of liquid inside the cavities and channel can be easily viewed from the side.

Figure 3A:
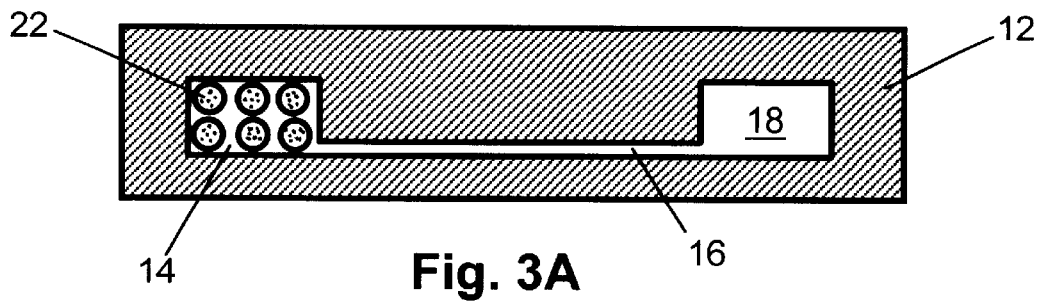
FIGS. 3A–E shows a schematic cross-section view of an example of a capillary test specimen, according to the present invention, illustrating the placement and melting of a solder or braze material, and the subsequent progression of the liquid front as it moves from left to right, out of the open source cavity, through the open capillary channel, and into the open fillet cavity, where it forms a fillet on upper and lower free surfaces.
Figure 3B:
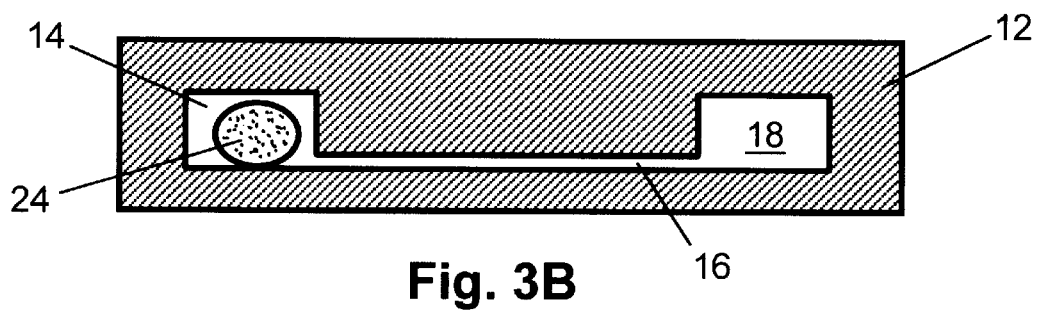
Figure 3C:
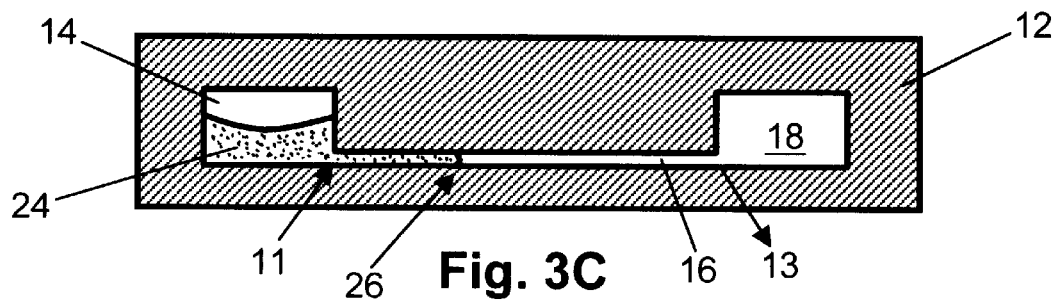
Figure 3D:
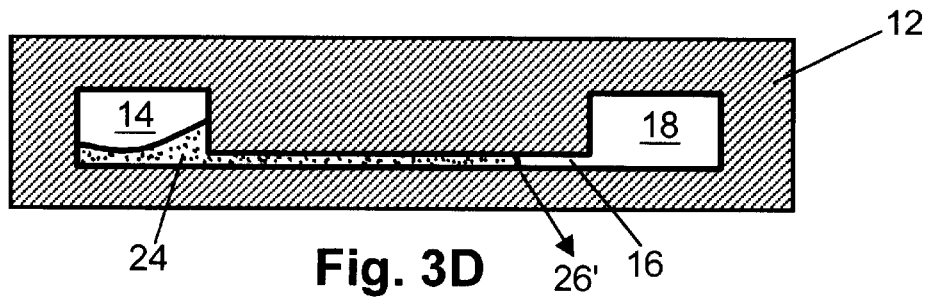
Figure 3E:
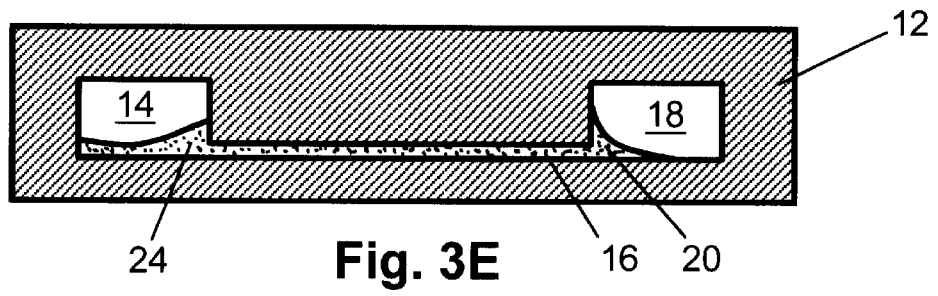

FIGS. 3A–3E shows a schematic cross-section view of an example of a capillary test specimen, according to the present invention, illustrating the placement and melting of a solder or braze material 22, and the subsequent progression of the liquid front 26 as it moves from left to right, out of the source cavity 14, through the capillary channel 16, and into the fillet cavity 18, where it forms a fillet 20 on upper and lower free surfaces of fillet cavity 18. In FIG. 3A, solid braze wires or preforms 22 have been pre-placed inside of source cavity 14, prior to melting. Next, in FIG. 3B, body 12 is heated to a temperature above the melting point of braze wires or preforms 22, which subsequently coalesce into a mass (e.g., a ball) of molten (i.e., liquid) braze material 24. Then, in FIG. 3C, liquid 24 wets the inside surfaces of source cavity 14 (for example, after dissolving a thin oxide layer), and touches entrance 11. Next, capillary forces drive liquid 24 from left to right towards exit 13. FIGS. 3C and 3D show snapshots of the motion of liquid 24 at two different liquid front positions, 26 and 26'. Finally, in FIG. 3E, liquid 24 has flowed into fillet cavity 18 and formed stable fillet 20 between two free surfaces. Body 12 can be subsequently cooled to solidify the braze material in a final, stable configuration.

Figure 4:
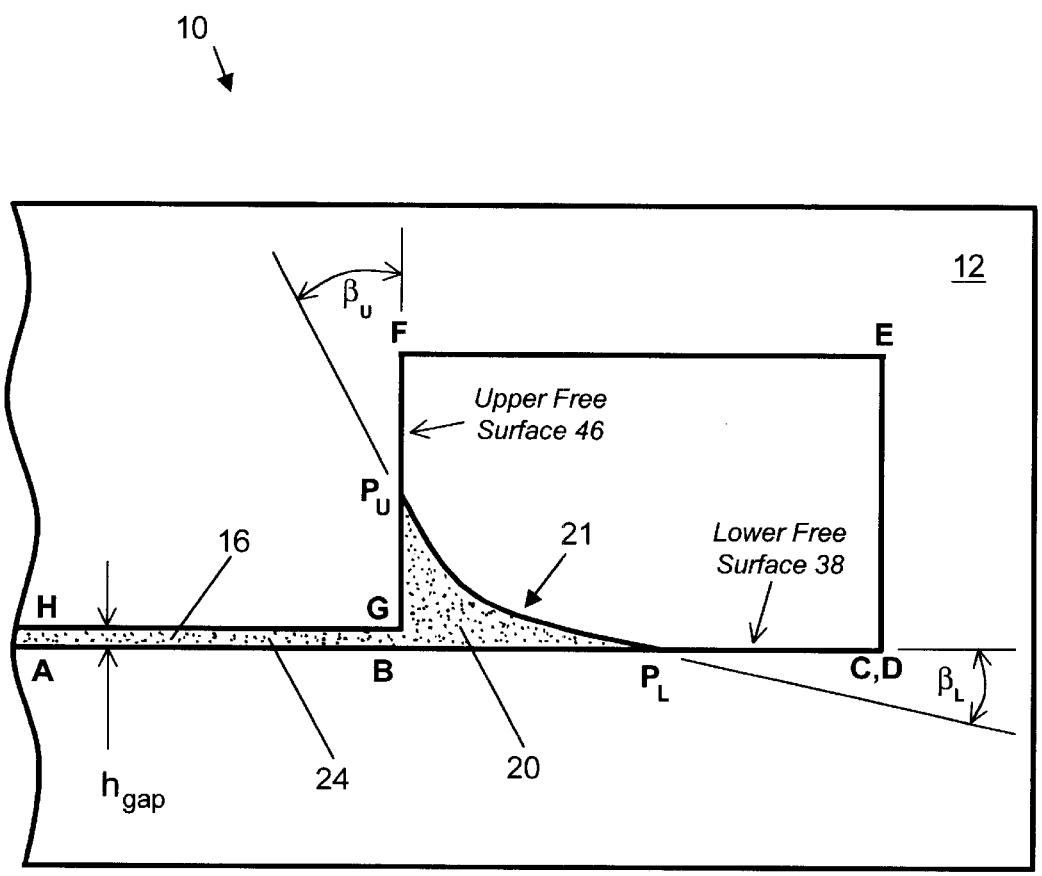
FIG. 4 shows a magnified schematic cross-section view of a liquid (or solidified) fillet that has formed inside of the fillet cavity, according to the present invention.

FIG. 4 shows a magnified schematic cross-section view of a liquid (or solidified) fillet that has formed inside of the fillet cavity, according to the present invention. Liquid 24 has flowed from left to right through capillary channel 16 into fillet cavity 18, where fillet 20 has formed. Fillet 20 has a fillet meniscus 21, whose end points are defined by lower pinning point, $P_L$, located on lower free surface 38, and upper pinning point, $P_U$, located on upper free surface 46. The angle that the lower end of fillet 20 makes with lower free surface 38 is called the lower contact angle, $\beta_{lower}$, and the angle that the upper end of fillet 20 makes with upper free surface 46 is called the upper contact angle, $\beta_{upper}$. In general, the better that liquid 24 wets the two free surfaces, the lower the contact angles $\beta_{lower}$ and $\beta_{upper}$ will be.

Figure 5A:
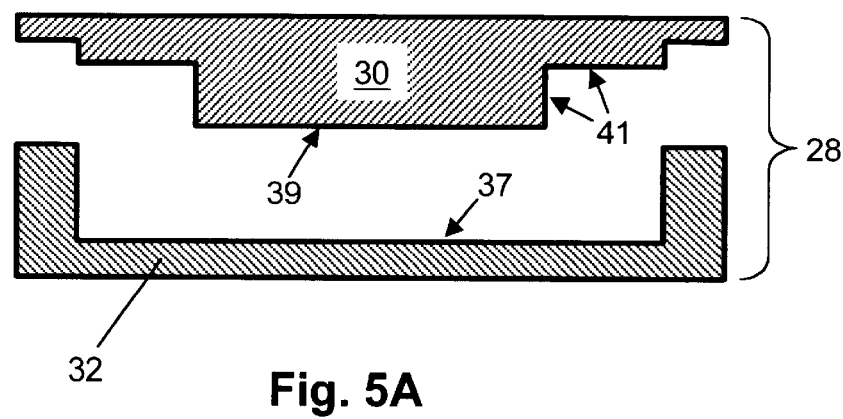
FIG. 5A shows an exploded, schematic cross-section view of an example of a two-piece capillary test specimen, according to the present invention.

FIG. 5A shows an exploded, schematic cross-section view of an example of a two-piece capillary test specimen, according to the present invention. Upper part 30 can rest on lower part 32 under the force of gravity, or they can be clamped together (not shown). Alternatively, they can be brazed or otherwise bonded together. Assembled test specimen 28 comprises the same source cavity 14, capillary channel 16, and fillet cavity 18 as shown, for example, in FIG. 2B.

Figure 5B:
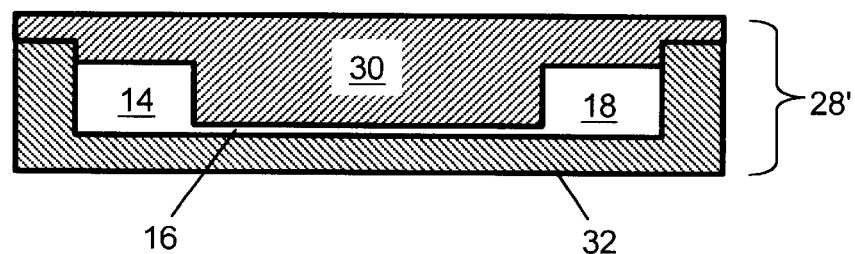
FIG. 5B shows a schematic cross-section view of an example of an assembled, two-piece capillary test specimen, according to the present invention.

FIG. 5B shows a schematic cross-section view of an example of an assembled, two-piece capillary test specimen, according to the present invention. Upper part 30 has been place together with lower part 32 to make assembled test specimen 28. Upper part 30 and lower part 32 can be made of the same, or different, material. For example, one part can be made of a metal and the other of a ceramic; or one part plastic and the other silicon, etc. Alternatively, both parts can be made of the same bulk material, but the interior surfaces 37 and 39, respectively, of lower part 32 and upper part 30 can be coated with the same, or different, materials to study the effects of different surface coatings or surface treatments (e.g., polished or roughened surfaces, anodized surfaces, etc.) on the liquid behavior during capillary flow and fillet formation (e.g., Ti, Zr, Hf active metal coatings, or Au noble coatings that can improve or inhibit flow). In principle, the interior surfaces 41 which comprise part or all of fillet cavity 18 (of assembled specimen 28) can be coated with a different material that is used to coat the interior surfaces of capillary channel 16 (e.g., surfaces 37 and 39 of assembled specimen 28), depending on the particular application. Optionally, upper part 30 (or, lower part 32) can be made of a transparent material, such as a clear plastic, glass, silica, quartz, or sapphire, to permit viewing of the flowing liquid down through the top (or up from the bottom) of the capillary test specimen. Optionally, upper part 30 (or lower part 32) can be made of an IR transparent material, such as silicon.

Figure 5C:
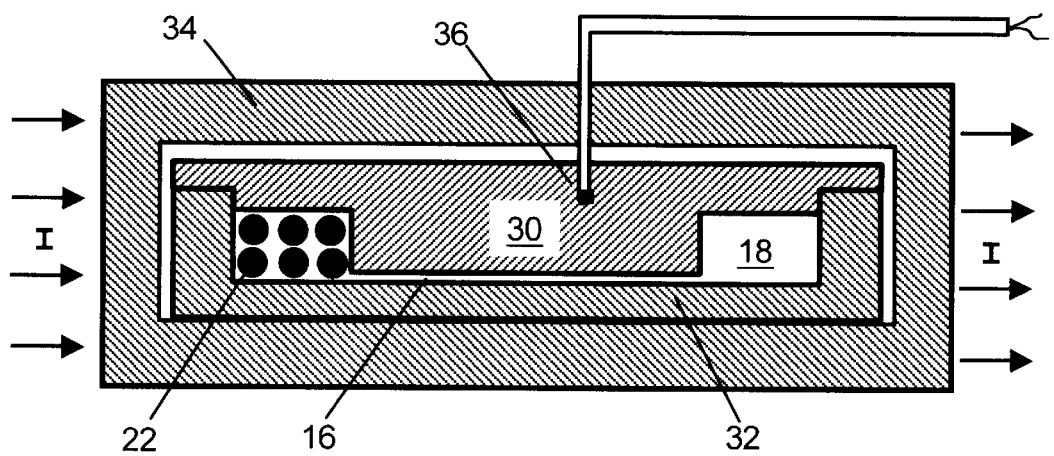
FIG. 5C shows a schematic cross-section view of an example of a two-piece capillary test specimen held inside of a specimen holder, with an thermocouple embedded in the upper piece for measuring temperature, and with electric current passing through the specimen holder for resistively heating the specimen holder and test specimen, according to the present invention.

FIG. 5C shows a schematic cross-section view of an example of a two-piece capillary test specimen held inside of a specimen holder, with an thermocouple embedded in the upper piece for measuring and controlling temperature, and with electric current, I, flowing through the specimen holder for resistively heating the specimen holder and test specimen, according to the present invention. Assembled test specimen 28 (comprising upper plate 30 mated to lower plate 32) has been placed inside of specimen holder 34. Specimen holder 34 is heated directly by electric resistance heating. Heated specimen holder 34 indirectly heats assembled test specimen 28 through a combination of conduction and radiation heat transfer, and electric resistance heating (there will likely be electrical contact between holder 34 and sample 30). Specimen holder 34, which has open front and back sides to permit visual access to the behavior of liquid 24 in capillary channel 16 and fillet cavity 18, can be heated in a variety of ways, including electric resistance heating by passing a high electric current, I, through the bulk of specimen holder 34. Alternatively, a laser beam, electron beam, or infrared radiation (including focused IR radiation) can be used to heat specimen holder 34, or, alternatively, to directly heat and melt braze wires or preforms 22. Thermocouple 36, embedded in upper plate 30, can be used to monitor temperatures during testing. Optionally, IR pyrometry . (not shown) can be used to monitor temperatures. Optionally, thermocouple 36 can be embedded in specimen holder 34. The location of the thermocouple can be changed to vary heating responses.

Electric resistance heating of specimen holder 34 can be accomplished by clamping or gripping both ends of specimen holder 34 with water-cooled, high-current carrying copper clamps or grips. By using a sufficiently large, high current power supply (e.g., thousands of amps), the temperature of specimen holder 34 can be raised from room temperature to 900 C in seconds or less. Thermocouple 36 can be used to provide information to the power supply for enabling feedback control of the current versus time profile, permitting accurate control of the heating and cooling rates to closely reproduce realistic heating/cooling cycles, including hold times at a constant temperature. A particularly useful machine for providing rapid electric resistance heating with feedback control is a Gleeble™ machine, manufactured by Dynamic Systems, Inc., which can heat a sample at 10,000 C/second. At elevated temperatures, where oxidation becomes a problem, a shroud assembly with a transparent glass (silica, quartz, etc.) or sapphire window can be placed around specimen holder 34 to confine a protective cover of inert gas, such as argon, nitrogen, or helium, which surrounds and protects the heated test specimen 10 or 28. Using this type of setup, a conventional heating furnace is not required. This reduces the time needed to perform a test from hours to minutes or seconds. Once the temperature reaches a point close to the melting point of the braze, a high-speed video or digital camera with magnifying optics can be activated to record the flowing liquid (which can flow with a velocity of about 5–10 mm/s).

Figure 6:
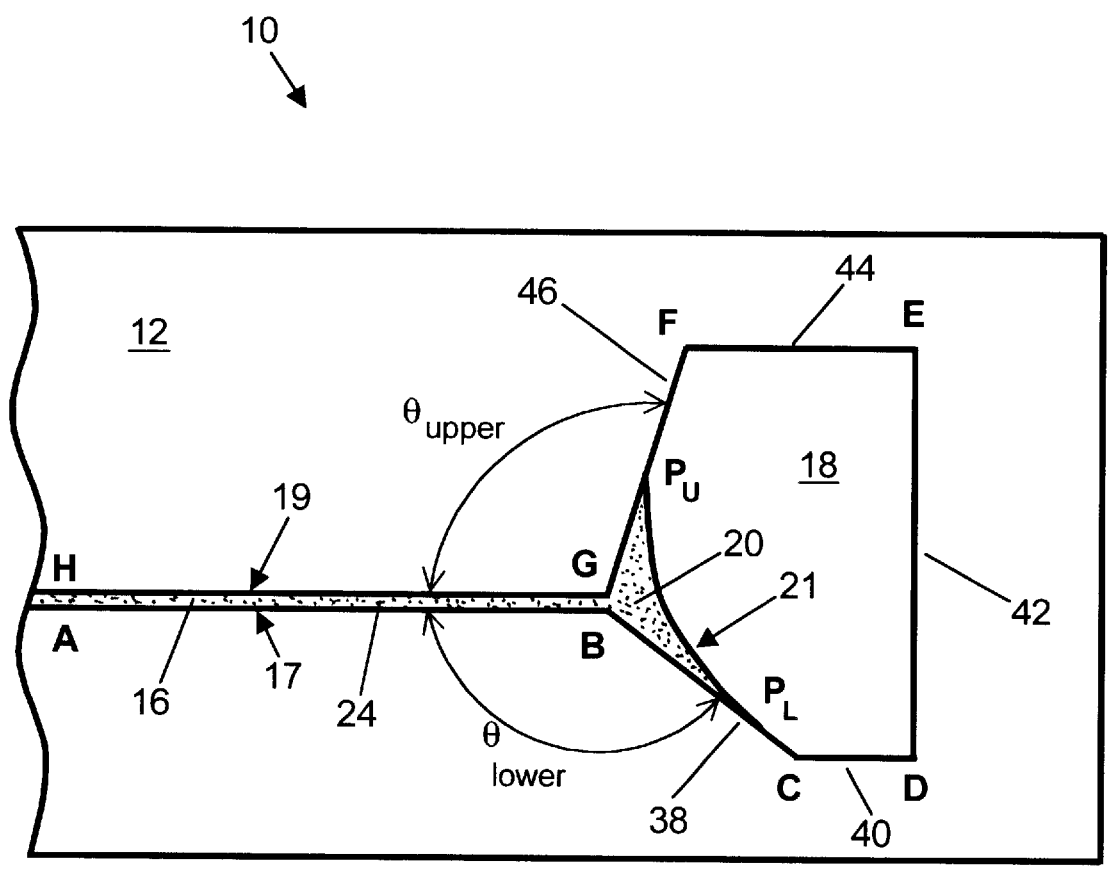
FIG. 6 shows a schematic cross-section view of an example of a capillary test specimen with an open fillet cavity having both upper and lower free surfaces inclined at non-right angles to the horizontal plane of the open capillary channel, according to the present invention.

FIG. 6 shows a schematic cross-section view of an example of a capillary test specimen with an open fillet cavity having both upper and lower free surfaces inclined at non-right angles to the horizontal plane of the open capillary channel, according to the present invention. The geometry of the interior, wetted surfaces of fillet cavity 18 can be selected and configured to closely simulate a geometrically complex, realistic braze joint geometry. In FIG. 6, fillet 20 wets lower free surface 38 and the upper free surface 46. Fillet cavity 18 is defined by connecting line segments BC, CD, DE, EF, and FG. Lower free surface 38 (i.e., segment BC) connects to the distal end of lower channel 17 at point B, while upper free surface 46 (i.e., segment EG) connects to the distal end of upper channel 19 at point G. The angle between lower free surface 38 and lower channel 17 ($\theta_{lower}$) can be greater than zero, but less than or equal to 180 degrees. Likewise, the angle between upper free surface 46 and upper channel surface 19 ($\theta_{upper}$) can be greater than zero, but less than or equal to 180 degrees. In FIG. 6, $\theta_{lower}$ is about 145 degrees, and $\theta_{upper}$ is about 110 degrees. When $\theta_{lower}$ equals 180 degrees, and $\theta_{upper}$ equals 90 degrees, then the geometry of fillet cavity 18 is the same as that shown in FIG. 2B.

Figure 7:
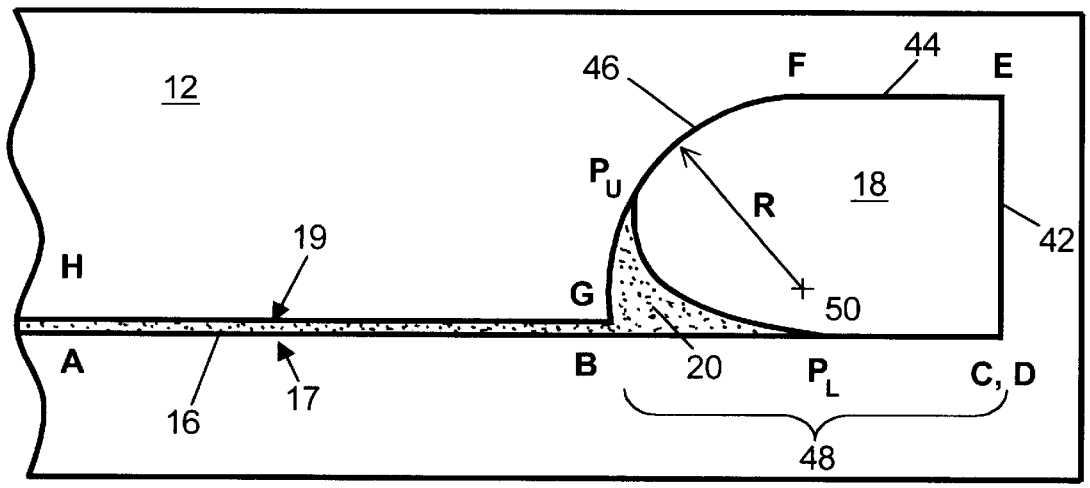
FIG. 7 shows a schematic cross-section view of another example of a capillary test specimen with an open fillet cavity having a curved upper free surface and a horizontal lower free surface, where the radius of curvature is located inside of the open fillet cavity, according to the present invention.

FIG. 7 shows a schematic cross-section view of another example of a capillary test specimen with an open fillet cavity having a curved upper free surface 46 and a horizontal lower free surface 48, where the radius of curvature is located inside of the open fillet cavity, according to the present invention. In this example, lower free surface 48 (segment BC) is horizontal and extends straight out from line segment AB. Upper free surface 46 (line segment FG) is a circular arc having a radius of curvature, R, and an origin 50 located inside of open fillet cavity 18.

Figure 8:
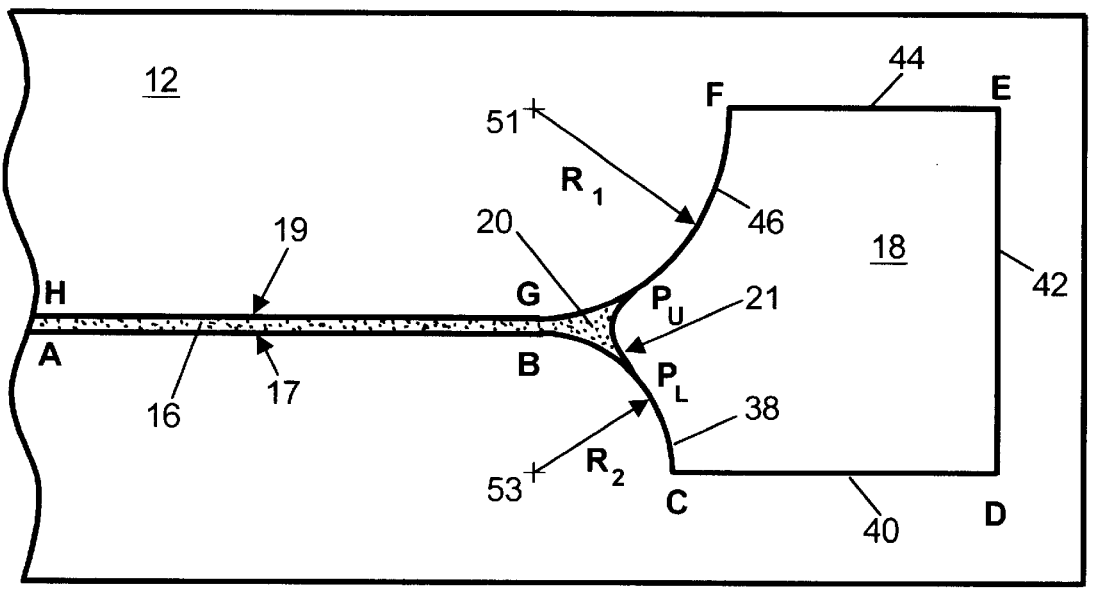
FIG. 8 shows a schematic cross-section view of another example of a capillary test specimen with an open fillet cavity having curved upper and lower free surfaces, where the radius of curvature for both surfaces are different, and their origins are located outside of the open fillet cavity, according to the present invention.

FIG. 8 shows a schematic cross-section view of another example of a capillary test specimen with an open fillet cavity having curved upper and lower free surfaces, where the radius of curvature for both surfaces are different, and where their origins are located outside of the open fillet cavity, according to the present invention. In this example, lower free surface line 48 (segment, BC) is a circular arc, extending straight out from line segment AB. Upper free surface 46 (line segment FG) is a circular arc having a first radius of curvature, $R_1$, with its origin 51 located outside of the fillet cavity. Lower free surface 46 (line segment BC) is a circular arc having a different radius of curvature, $R_2$, with its origin 53 located outside of the fillet cavity. In this example, $R_1 > R_2$.

Figure 9:
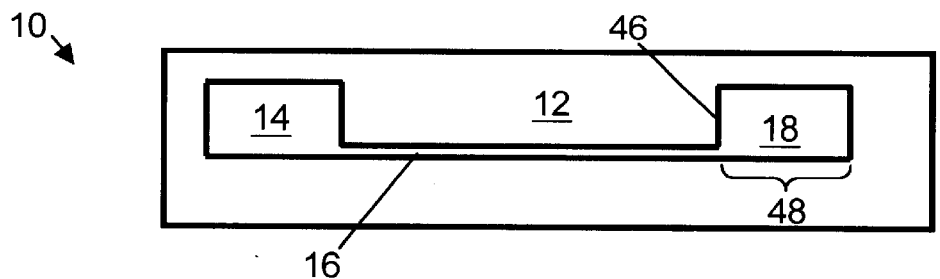
FIG. 9 shows a schematic cross-section view of another example of a capillary test specimen, according to the present invention.

FIG. 9 shows a schematic cross-section view of another example of a capillary test specimen, according to the present invention. In this example, fillet cavity 18 has a rectangular shape that matches the shape of the source cavity 14. Here, the upper surface 46 is straight with $\theta_{upper}$=90 degrees, and the lower surface 48 is straight with $\theta_{lower}$=180 degrees.

Figure 10:
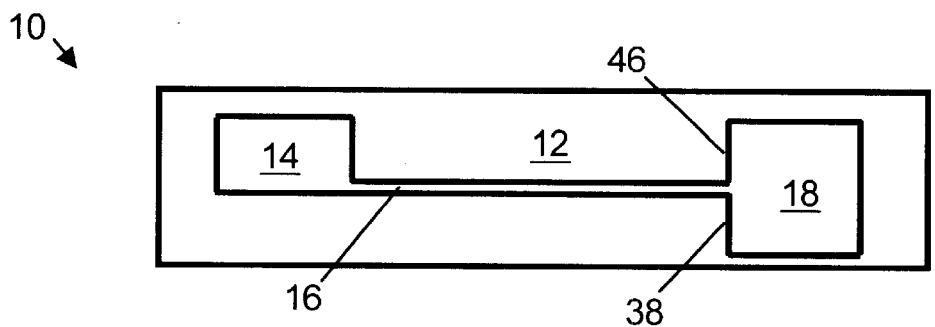
FIG. 10 shows a schematic cross-section view of another example of a capillary test specimen, according to the present invention.

FIG. 10 shows a schematic cross-section view of another example of a capillary test specimen, according to the present invention. In this example, $\theta_{upper}$=90 degrees, and $\theta_{lower}$=90 degrees.

Figure 11:
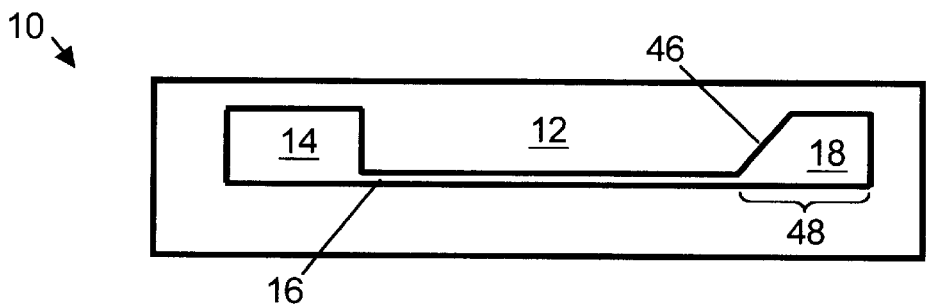
FIG. 11 shows a schematic cross-section view of another example of a capillary test specimen, according to the present invention.

FIG. 11 shows a schematic cross-section view of another example of a capillary test specimen, according to the present invention. In this example, $\theta_{upper}$>90 degrees, and $\theta_{lower}$=180 degrees. In other words, the included angle between the upper and lower free surfaces 46 and 48, respectively, is less than 90 degrees.

Figure 12:
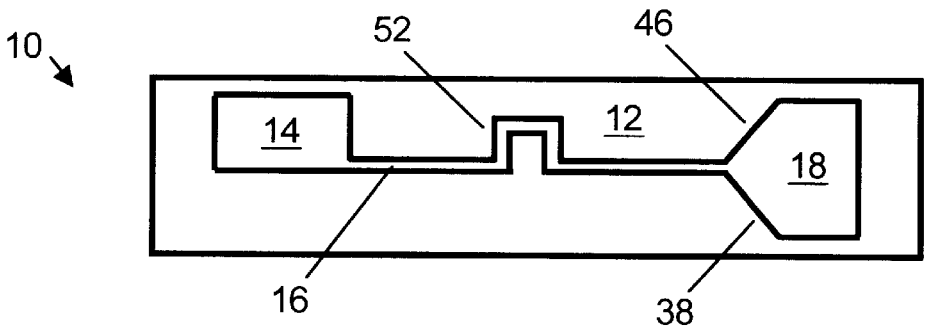
FIG. 12 shows a schematic cross-section view of another example of a capillary test specimen, according to the present invention.

FIG. 12 shows a schematic cross-section view of another example of a capillary test specimen, according to the present invention. In this example, $\theta_{upper}$=$\theta_{lower}$, and both are greater than 90 degrees. Additionally, capillary channel 16 has a kinked segment 52 (inverted u-shaped bend), which acts as a flow restriction in channel 16. Other types of restrictions in the capillary channel can be envisioned.

Figure 13:
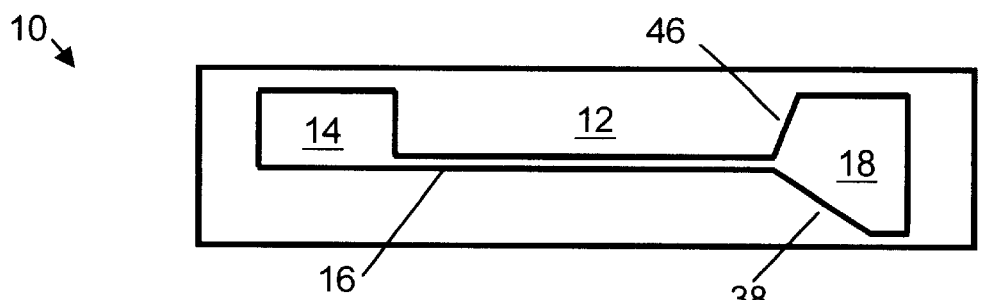
FIG. 13 shows a schematic cross-section view of another example of a capillary test specimen, according to the present invention.

FIG. 13 shows a schematic cross-section view of another example of a capillary test specimen, according to the present invention. In this example, both $\theta_{upper}$ and $\theta_{lower}$ are greater than 90 degrees, and $\theta_{upper} < \theta_{lower}$.

Figure 14:
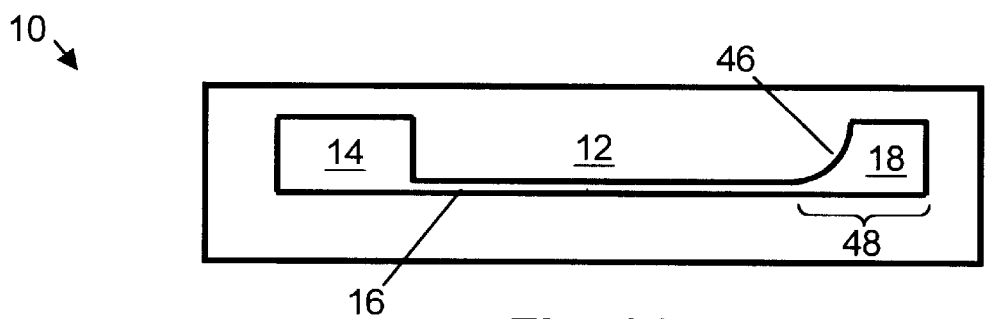
FIG. 14 shows a schematic cross-section view of another example of a capillary test specimen, according to the present invention.

FIG. 14 shows a schematic cross-section view of another example of a capillary test specimen, according to the present invention. In this example, upper surface 46 is curved with the origin point of the radius of curvature being located outside of fillet cavity 18, and $\theta_{lower}$=180 degrees.

Figure 15:
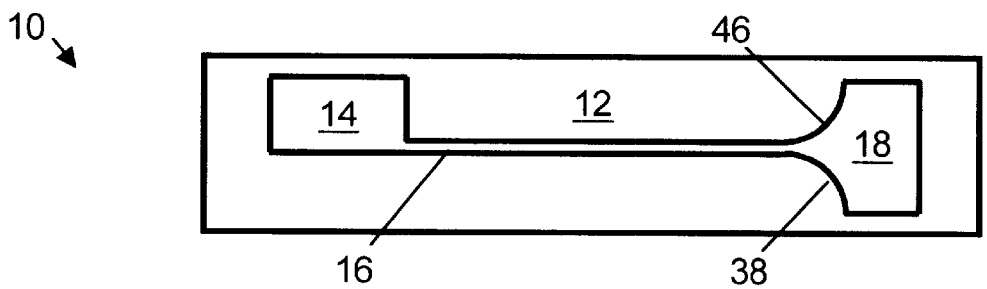
FIG. 15 shows a schematic cross-section view of another example of a capillary test specimen, according to the present invention.

FIG. 15 shows a schematic cross-section view of another example of a capillary test specimen, according to the present invention. In this example, upper surface 46 is curved with the origin point of the radius of curvature being located outside of fillet cavity 18, and the lower surface 38 is curved with the origin point of the radius of curvature being located outside of fillet cavity 18, and the two radii of curvatures are the same.

Figure 16:
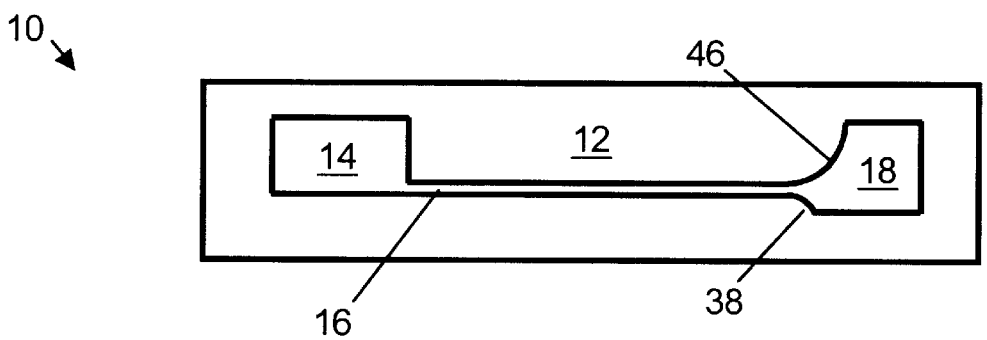
FIG. 16 shows a schematic cross-section view of another example of a capillary test specimen, according to the present invention.

FIG. 16 shows a schematic cross-section view of another example of a capillary test specimen, according to the present invention. In this example, upper surface 46 is curved with the origin point of the radius of curvature being located outside of fillet cavity 18, and the lower surface 38 is curved with the origin point of its radius of curvature being located outside of fillet cavity 18, and the upper radius of curvature is greater than the lower radius of curvature.

Figure 17:
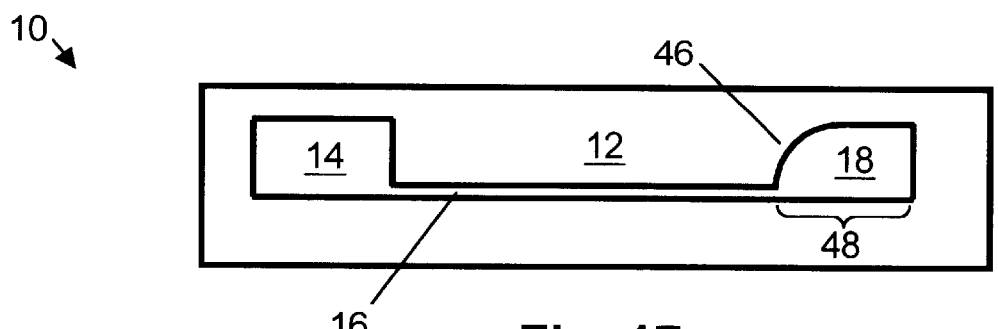
FIG. 17 shows a schematic cross-section view of another example of a capillary test specimen, according to the present invention.

FIG. 17 shows a schematic cross-section view of another example of a capillary test specimen, according to the present invention. In this example, upper surface 46 is curved with the origin point of the radius of curvature being located inside of fillet cavity 18, and $\theta_{lower}$=180 degrees.

Figure 18:
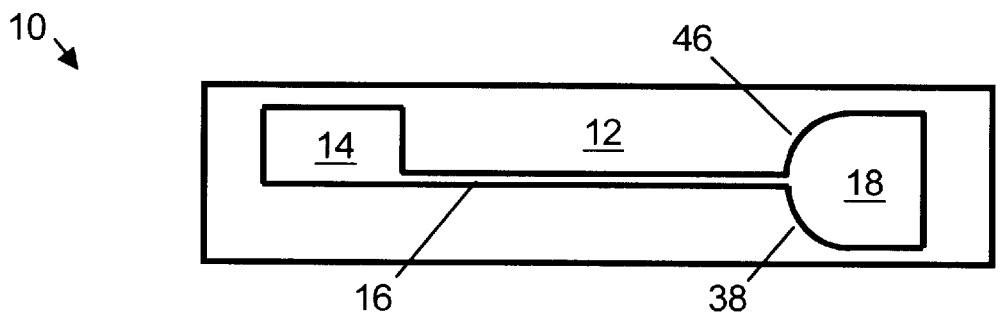
FIG. 18 shows a schematic cross-section view of another example of a capillary test specimen, according to the present invention.

FIG. 18 shows a schematic cross-section view of another example of a capillary test specimen, according to the present invention. In this example, upper surface 46 is curved with the origin point of the radius of curvature being located inside of fillet cavity 18. Lower surface 38 is curved with the origin point of the radius of curvature being located inside of fillet cavity 18, and the two radii of curvatures are equal.

Figure 19:
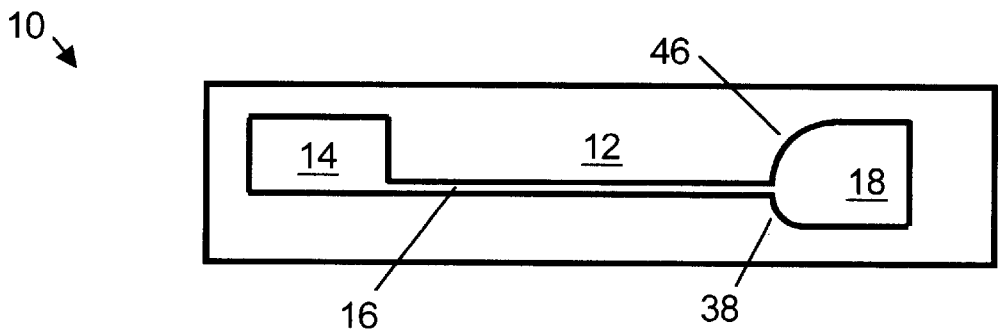
FIG. 19 shows a schematic cross-section view of another example of a capillary test specimen, according to the present invention.

FIG. 19 shows a schematic cross-section view of another example of a capillary test specimen, according to the present invention. In this example, upper surface 46 is curved with the origin point of the radius of curvature being located inside of fillet cavity 18. Lower surface 38 is curved with the origin point of the radius of curvature being located inside of fillet cavity 18, and the upper radius of curvature is greater than the lower radius of curvature.

Figure 20:
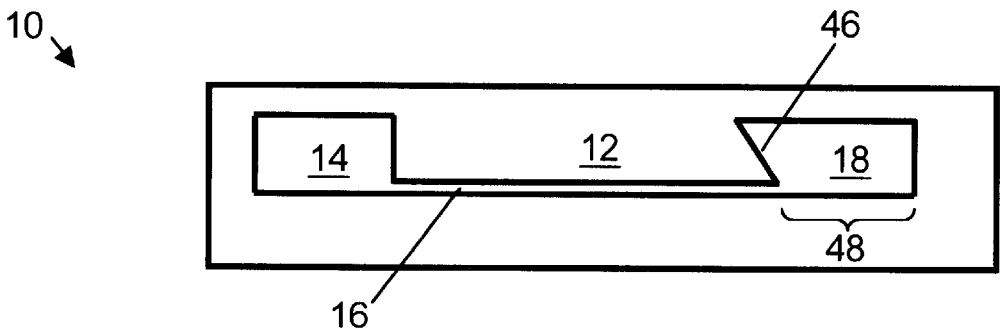
FIG. 20 shows a schematic cross-section view of another example of a capillary test specimen, according to the present invention.
Figure 21:
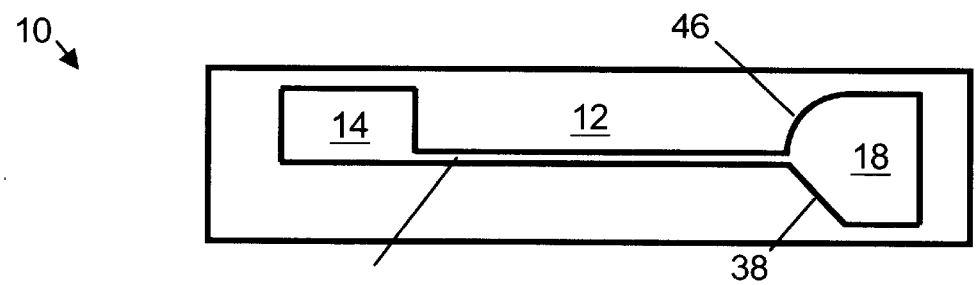
FIG. 21 shows a schematic cross-section view of another example of a capillary test specimen, according to the present invention.

FIG. 20 shows a schematic cross-section view of another example of a capillary test specimen, according to the present invention. In this example, $\theta_{lower}$<90 degrees and $\theta_{lower}$=180 degrees FIG. 21 shows a schematic cross-section view of another example of a capillary test specimen, according to the present invention. In this example, upper surface 46 is curved with the origin point of the radius of curvature being located inside of fillet cavity 18, and the lower surface 38 is straight with $\theta_{lower}$>90 degrees.

Figure 22:
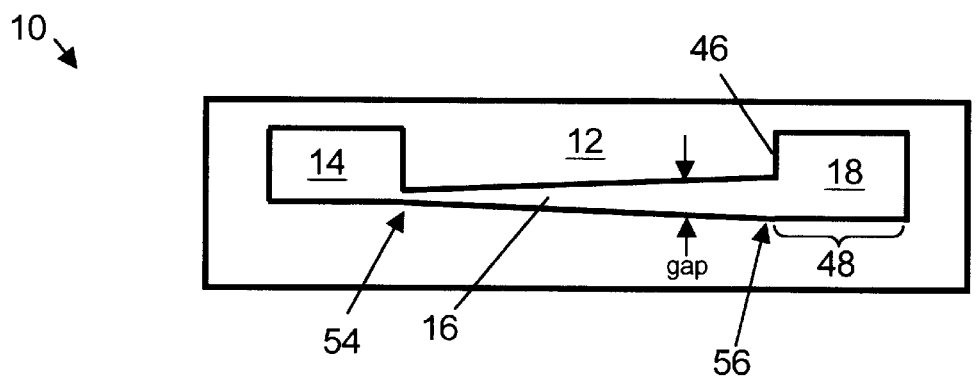
FIG. 22 shows a schematic cross-section view of another example of a capillary test specimen, according to the present invention.

FIG. 22 shows a schematic cross-section view of another example of a capillary test specimen, according to the present invention. In this example, the capillary gap, $h_{gap}$, of capillary channel 16 is non-uniform, and increases linearly from entrance 54 to exit 56 along channel 16.

Figure 23:
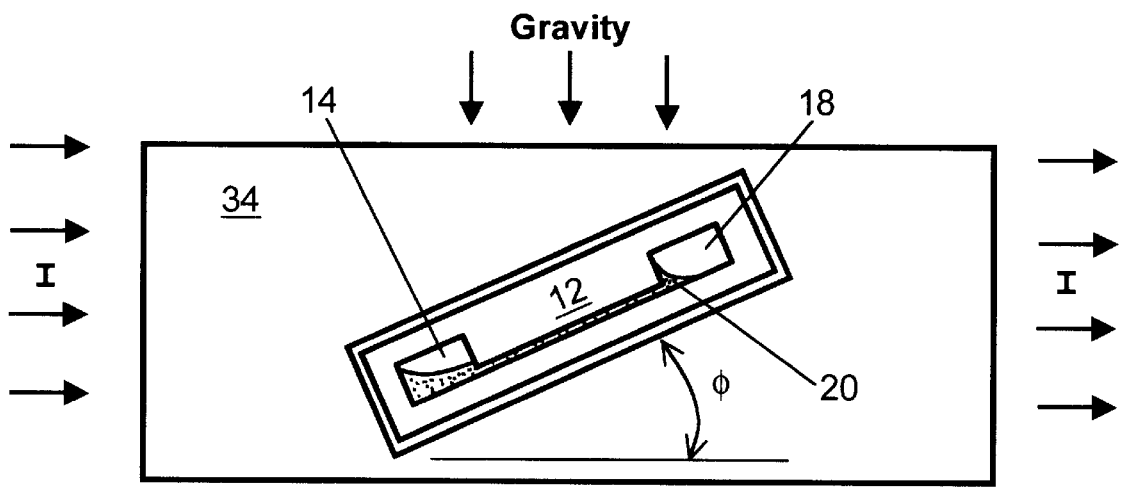
FIG. 23 shows a schematic cross-section view of an example of a capillary test specimen held inside of a specimen holder at an inclined angle, $\phi$, with respect to the direction of gravity, according to the present invention.

FIG. 23 shows a schematic cross-section view of an example of a capillary test specimen 12 held inside of a specimen holder 34 at an inclined angle φ with respect to the direction of gravity that is greater than zero, but less than 90 degrees, according to the present invention. Inclining the test specimen allows the effect of gravitational forces to be studied on the capillary flow in capillary channel 16, and on the formation of fillet 20 in filet cavity 18.

Figure 24:
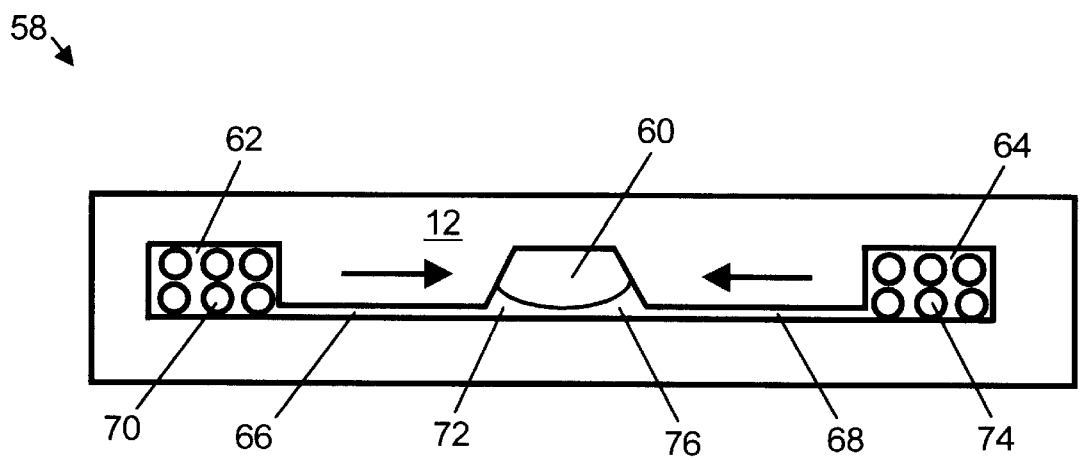
FIG. 24 shows a schematic cross-section view of an example of a capillary test specimen having two different open source cavities connected to an open fillet cavity located in-between the two source cavities, according to the present invention.

FIG. 24 shows a schematic cross-section view of an example of a capillary test specimen having two different source cavities connected to a fillet cavity located in-between the two source cavities, according to the present invention. Fillet cavity 60 is disposed in-between left source cavity 62 and right source cavity 64. Fillet cavity 60 is fluidically connected to left source cavity 62 by left capillary channel 66. Fillet cavity 60 is fluidically connected to right source cavity 64 by right capillary channel 68. Braze wires or preforms 70 and 74 can be pre-placed in source cavities 62 and 64, respectively, prior to melting. Braze wires or preforms 70 and 74 can be made of the same, or different, braze material. Fillets 72 and 76 can touch each other inside of fillet cavity 60, or not, depending on the conditions.

Figure 25:
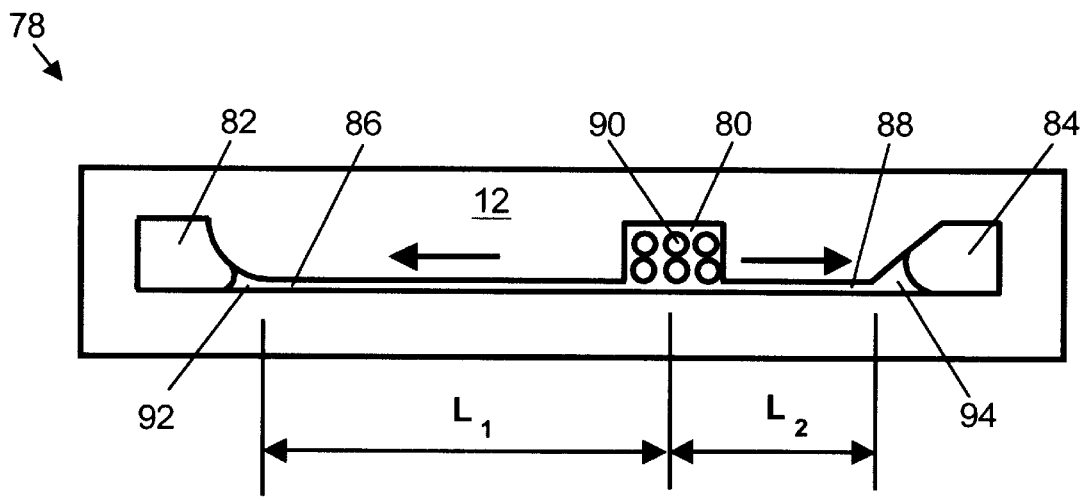
FIG. 25 shows a schematic cross-section view of an example of a capillary test specimen having two different open fillet cavities connected to a single open source cavity located at different distances in-between the two open fillet cavities, according to the present invention.

FIG. 25 shows a schematic cross-section view of an example of a capillary test specimen having two different open fillet cavities connected to a single open source cavity located at different distances in-between the two open fillet cavities, according to the present invention. Source cavity 80 is disposed in-between left open fillet cavity 82 and right open fillet cavity 84. Source cavity 80 is fluidically connected to left open fillet cavity 82 by left open capillary channel 86. Source cavity 80 is fluidically connected to right open fillet cavity 84 by right open capillary channel 88. Braze wires or preforms 90 can be pre-placed in open source cavity 80 prior to melting. The length of the two different open capillary channels 86 and 88 can be the same, or different. In this example, $L_1$>$L_2$. The shape of the two different open fillet cavities 82, 84 can be the same, or different.

Figure 26A:
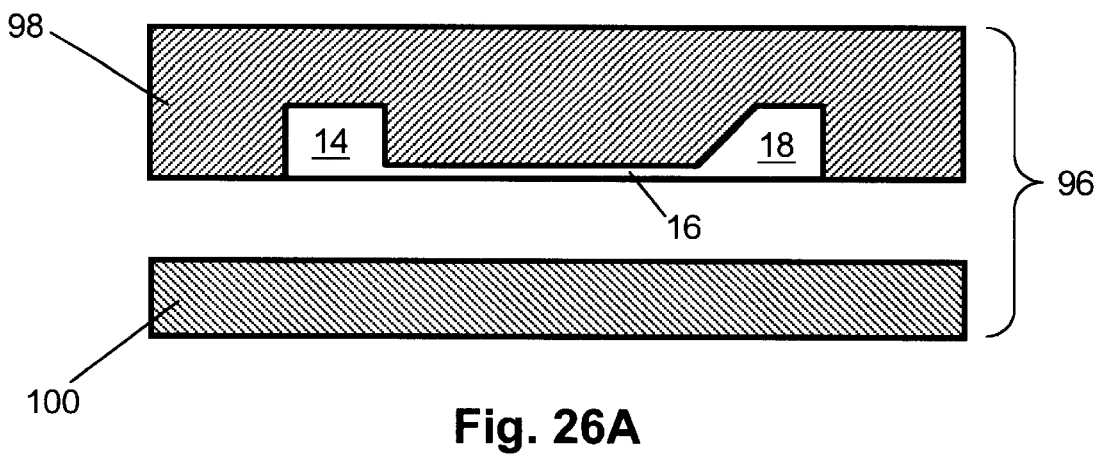
FIG. 26A shows an exploded, schematic cross-section view of another example of a two-piece capillary test specimen, according to the present invention.

FIG. 26A shows an exploded, schematic cross-section view of another example of a two-piece capillary test specimen, according to the present invention. Upper part 98 has been fabricated (e.g., machined, molded, cast, EDM wire cut, etc.) to completely contain source cavity 14, capillary channel 16, and fillet cavity 18. Lower part 100 is a flat closeout plate that when mated to upper part 98 forms completely assembled test specimen 96.

Figure 26B:
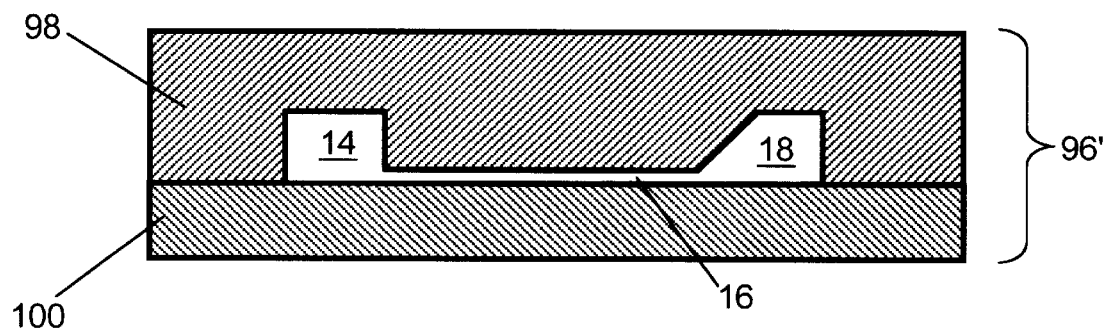
FIG. 26B shows a schematic cross-section view of another example of an assembled, two-piece capillary test specimen, according to the present invention.

FIG. 26B shows a schematic cross-section view of another example of an assembled, two-piece capillary test specimen, according to the present invention. Flat closeout plate 100 has been mated to upper part 98, thereby forming completely assembled test specimen 96', including source cavity 14, capillary channel 16, and fillet cavity 18. Upper part 98 and lower part 100 can be made of the same, or different, material. Upper part 98 and lower part 100 can made with the same material and coated with different materials on their interior surfaces (as discussed previously).

Figure 27:
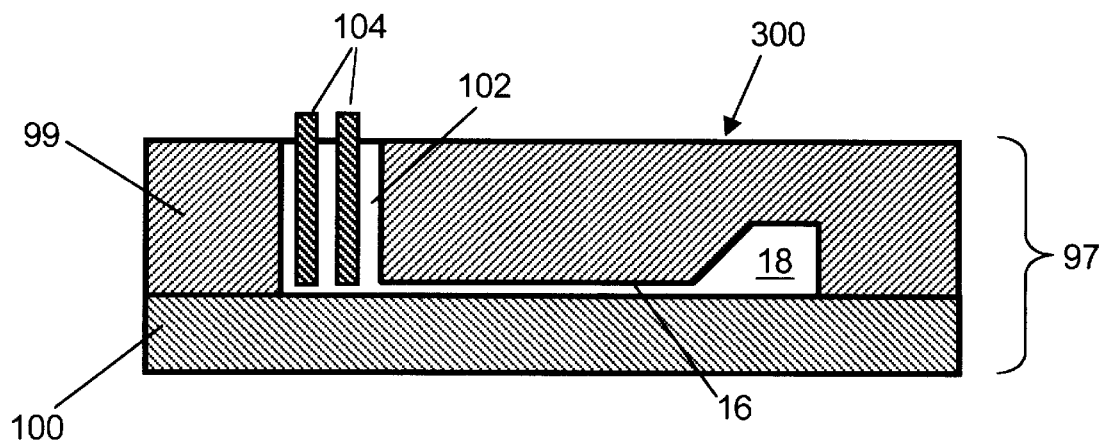
FIG. 27 shows a schematic cross-section view of another example of a two-piece capillary test specimen, where the source material is fed from the top instead of being fed from the side, according to the present invention.

FIG. 27 shows a schematic cross-section view of another example of a two-piece capillary test specimen, where the source material is fed from the top instead of being fed from the side, according to the present invention. Here, braze wire or preform 104 is pre-placed in source cavity 102 from the top surface 300 of upper part 99, rather than from an open side.

Figure 28:
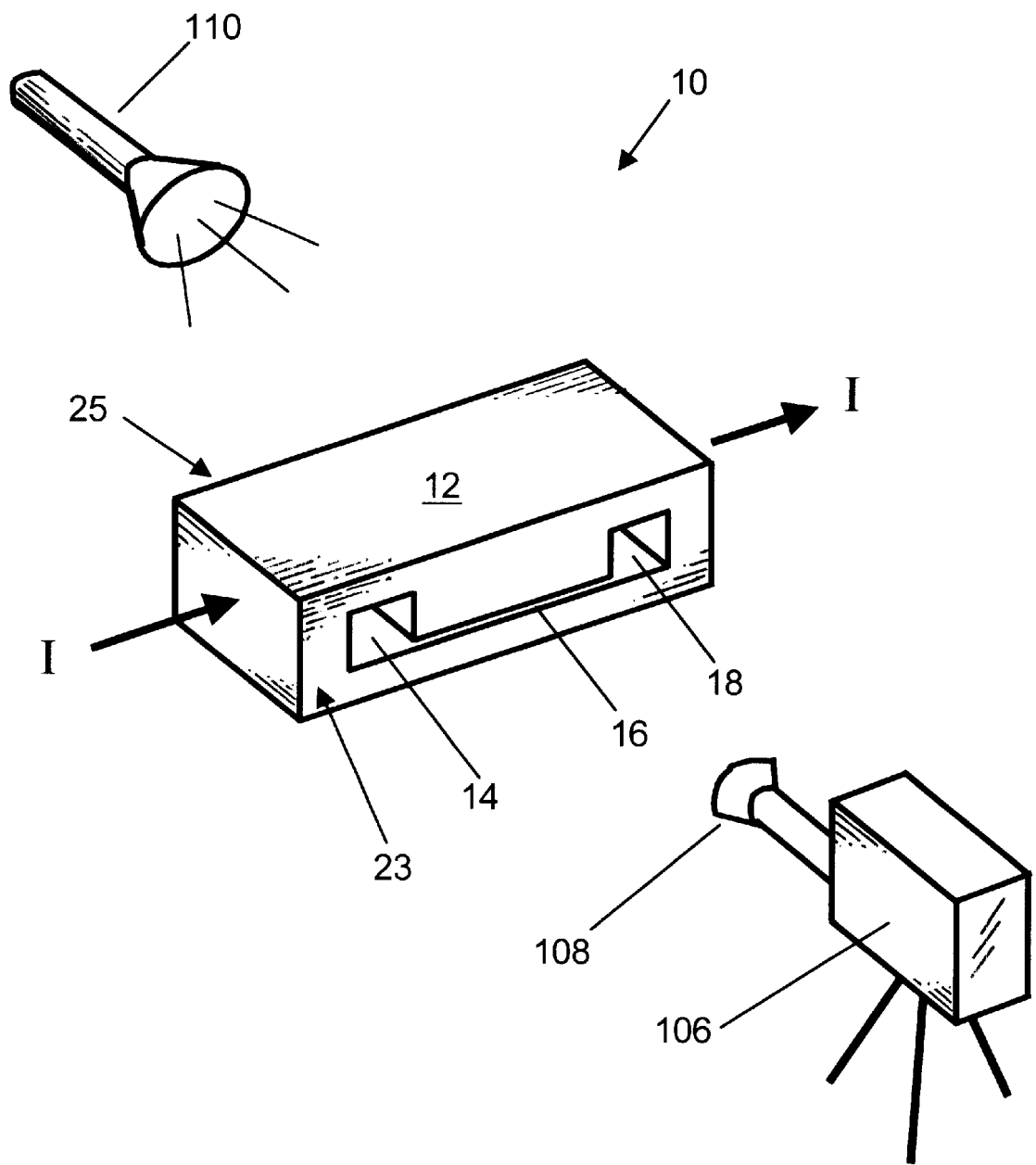
FIG. 28 shows a schematic isometric view of an example of a system for viewing the open side of a capillary test specimen with a video or digital camera, wherein the specimen is backlit from the opposite side with a light source, according to the present invention.

FIG. 28 shows a schematic isometric view of an example of a system for viewing the open side of a capillary test specimen with a video camera, wherein the specimen is backlit from the opposite side with a light source, according to the present invention. Capillary test specimen 10 comprises an open source cavity 14 fluidically connected to an open capillary channel 16 fluidically connected to an open fillet cavity 18. Open source cavity 14, open capillary channel 16, and open fillet cavity 18 penetrate completely through specimen 10 from frontside 23 to backside 25. Light source 110 illuminates backside 25 of specimen 10. High-speed video or digital camera 106 with magnifying optics 108 is oriented to view the frontside 23 of specimen 10. An electric current passes through the body of specimen 10 to rapidly heat it by electric resistance heating. Optionally, a protective inert gas cover can be placed around specimen 10 to prevent undesirable oxidation during high temperature exposure to air. A transparent window can be used to permit viewing of the test specimen. High-speed camera 106 can have a framing rate of from about 250 to 2000 frames per second. Camera 106 can be operated at high-speed just before the time when the braze material melts, so as to minimize the memory required for storing images (i.e., frames). A typical buffer imaging limit is 8000 frames, which is sufficient to record a total of 2000 frames over 4 seconds at a framing rate of 2000 frames/second. Camera 106 can comprise a CCD detector capable of viewing test specimen 10 in the optical, infrared, and/or UV spectrum.

Figure 29:
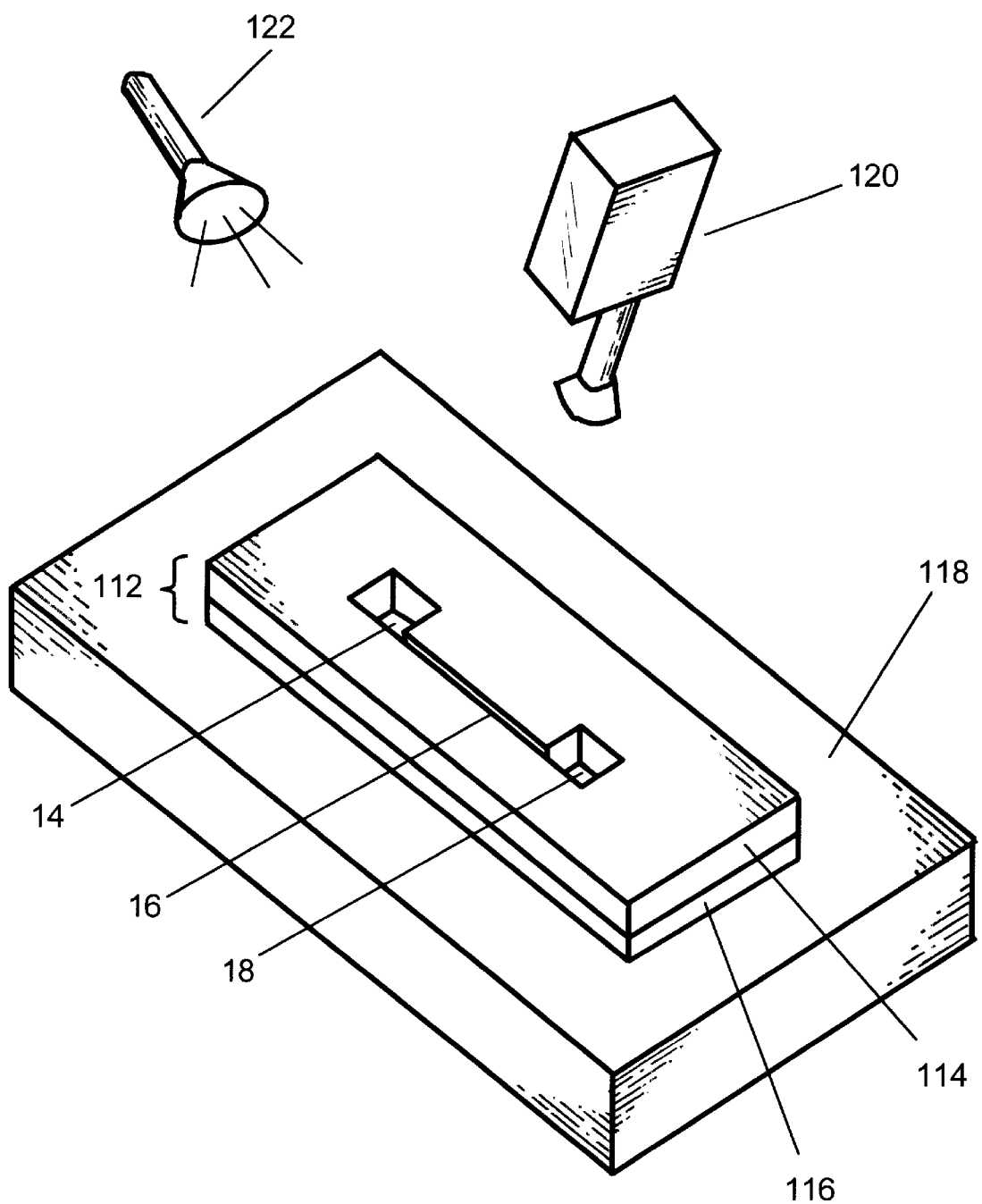
FIG. 29 shows a schematic isometric view of an example of a system for viewing the front side of a capillary test specimen with a video or digital camera, wherein the specimen rests on a flat hot plate, and is illuminated from the front with a light source, according to the present invention.

FIG. 29 shows a schematic isometric view of another example of a system for viewing the front side of a capillary test specimen with a video or digital camera, wherein the specimen rests on a flat hot plate and is illuminated from the front with a light source, according to the present invention. Test specimen 112 rests on a hot plate 118. Light source 122 illuminates specimen 112 from the topside, and camera 120 views light reflected from the topside of specimen 112. Test specimen 112 comprises top plate 114 disposed above bottom plate 116. Open source cavity 14, open capillary channel 16, and open fillet cavity 18 extend completely through top plate 114. Bottom plate 116 is a flat closeout plate. The two plates can be joined together to prevent liquid from seeping out from in-between the two plates. The assembled two-piece test specimen 112 is open on only one side, (as opposed to the test specimen shown in FIG. 27, which is open on both sides). Optionally, a still camera, an optical microscope, or a scanning electron beam microscope (SEM) can be used in place of video or digital camera 120.

Image processing software can be used to post-process the "grabbed" or "captured" images of the liquid flow in the capillary test specimen and extract quantitative information about the flow velocity, fillet meniscus shape, fillet contact angles, braze front profile, temperature distributions (in conjunction with the thermocouple data), shrinkage, and residual strains can be measured as a function of time.

Figure 30:
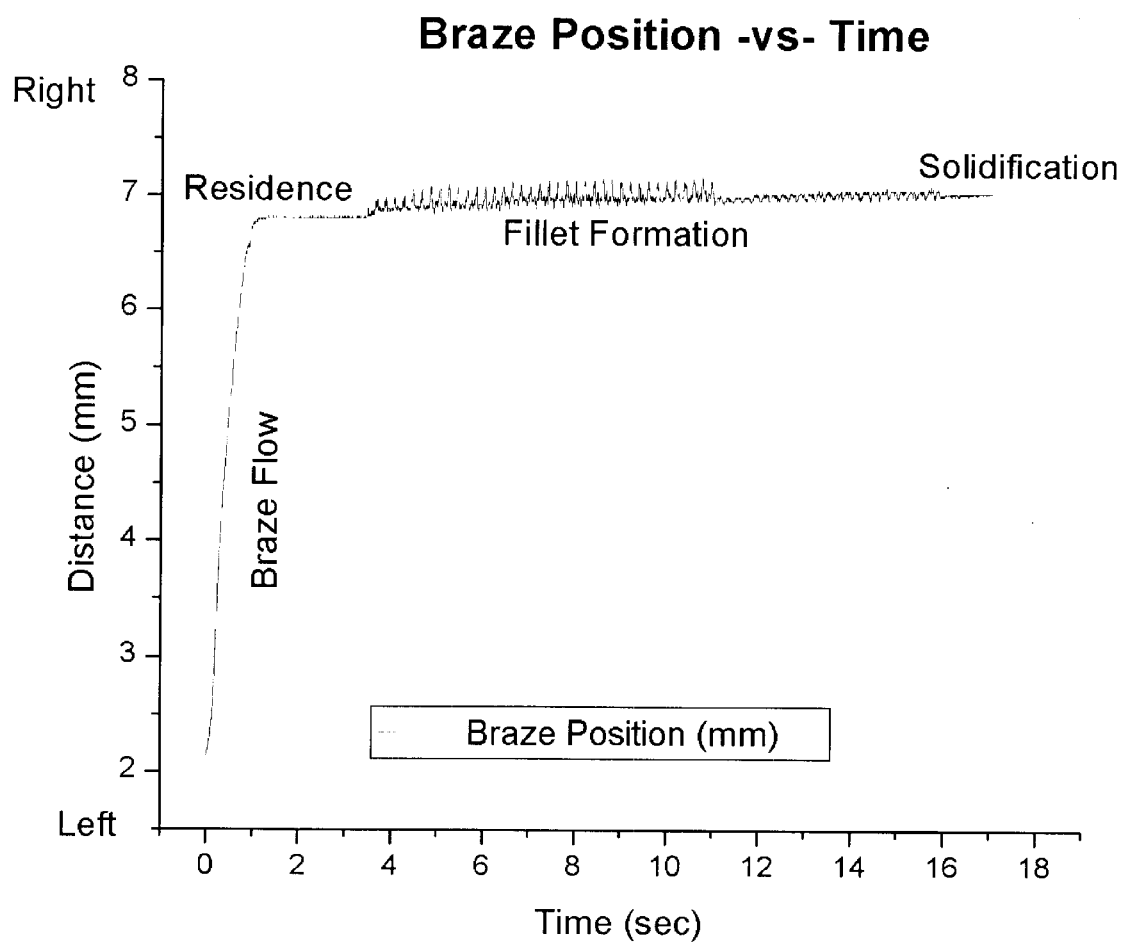
FIG. 30 shows experimental results using a test specimen similar to the one shown in FIG. 9, according to the present invention. The plot shows the position of the braze front as a function of time.

FIG. 30 shows experimental results using a test specimen similar to the one shown in FIG. 9, according to the present invention. FIG. 30 plots the position of the liquid braze front as a function of time as it flows through an open capillary channel and into an open fillet cavity. This experiment was performed using a monolithic capillary test specimen similar to the one shown in FIG. 9. A Gleeble™ 3500 system was used to resistively heat a specimen holder from room temperature to 750 C in 45 seconds; followed by a hold at 750 C for 15 seconds; followed by heating the specimen to 950 C in 12 seconds; followed by a 5 second hold at 950 C; followed by a cooldown period. The base metal of the test specimen was made of stainless steel alloy 304L. The braze alloy used was WESGO alloy CuSil (AWG Bag-20), a eutectic alloy of silver-copper, with a melting range point of 780 C, in the form of braze wires with a diameter of 0.020 inches. At 780 C the braze alloy is liquid. Labview™ software was used to post-process the "grabbed" images, which generated the position of the advancing capillary front of flowing liquid braze as a function of time as it flowed through the capillary channel and into the fillet cavity. FIG. 30 shows that the liquid front flowed a total of approximately 5 mm over a period of 1 sec, giving a flow velocity of about 5 mm/s. Flow stopped briefly for about 3 seconds at the entrance to the fillet cavity, and then flowed into the fillet cavity forming a fillet. The position of the fillet's meniscus was observed to oscillate rapidly over a period of about 10 seconds, at which point cooldown began and the liquid braze solidified. The cause of the rapid meniscus oscillations is unknown, but it is believed that this is the first experimental observation of this phenomenon.

The particular examples discussed above are cited to illustrate particular embodiments of the invention. Other applications and embodiments of the apparatus and method of the present invention will become evident to those skilled in the art.

The actual scope of the invention is defined by the claims appended hereto.

What is claimed is:

1. A test specimen for evaluating the behavior of a liquid inside an open capillary channel fluidically connected to an open fillet cavity, comprising:
    a solid body having a front side and an opposing back side;
    an open capillary channel disposed in the body, having an entrance and an exit;
    a source cavity disposed in the body and fluidically connected to the entrance of the open capillary channel; and
    an open fillet cavity disposed in the body and fluidically connected to the exit of the open capillary channel;
    wherein at least one side of the open capillary channel is open for permitting viewing into, and;
    wherein at least one side of the open fillet cavity is open for permitting viewing into.

2. The test specimen of claim 1, wherein the open capillary channel has a capillary gap between two opposing surfaces less than or equal to about 0.005 inches.

3. The test specimen of claim 1, wherein the open capillary channel has a capillary gap between two opposing surfaces whose magnitude varies linearly as a function of the distance along the channel.

4. The test specimen of claim 1, wherein the source cavity, the open capillary channel, and the open fillet cavity all extend completely through the body from the front side to the opposing back side.

5. The test specimen of claim 1, wherein the orientation of the open capillary channel with respect to the direction of gravity is inclined at an angle greater than zero degrees.

6. The test specimen of claim 1, wherein the volume of the source cavity is greater than the volume of the open capillary channel.

7. The test specimen of claim 1, wherein the body comprises an upper part and a lower part; and wherein the lower part has a cross-sectional profile selected from the group consisting of a flat profile and a U-shaped profile.

8. The test specimen of claim 7, wherein the upper part is made of a different material than the lower part.

9. The test specimen of claim 7, wherein the upper part comprises an optically transparent material selected from the group consisting of silica, quartz, and sapphire.

10. The test specimen of claim 7, wherein the upper comprises an IR transparent material comprising silicon.

11. The test specimen of claim 1, wherein the front side and the opposing back side of the body comprise a non-wetting or non-reacting surface selected from the group consisting of a polished surface and a surface coated with a non-wetting or non-reacting material.

12. The test specimen of claim 1, wherein the shape of the open fillet cavity comprises a rectangle when viewed from an open side.

13. The test specimen of claim 1, wherein the fillet cavity comprises two free surfaces upon which a fillet can form; and further wherein the included angle between the two free surfaces is less than 90 degrees.

14. A system for observing the flow of a liquid in a test specimen, comprising:
    a test specimen, comprising:
        a solid body having a front side and an opposing back side;
        an open capillary channel disposed in the body, having an entrance and an exit;
        a source cavity disposed in the body and fluidically connected to the entrance of the open capillary channel; and
        an open fillet cavity disposed in the body and fluidically connected to the exit of the open capillary channel;
        wherein at least one side of the open capillary channel is open for permitting viewing into, and;
        wherein at least one side of the open fillet cavity is open for permitting viewing into; and
    a high-speed imaging system with magnifying optics, facing at least one open side of the test specimen.

15. The system of claim 14, further comprising electrical resistance means for heating the test specimen.

16. The system of claim 15, wherein the electrical resistance heating means comprises a Gleeble™ machine.

17. The system of claim 14, further comprising a thermocouple embedded in the solid body for measuring the temperature of the test specimen.

18. A method for observing the flow of a liquid inside a test specimen, comprising:
    a) providing a test specimen comprising;
        a solid body having a front side and an opposing back side;
        an open capillary channel disposed in the body, having an entrance and an exit;
        a source cavity disposed in the body and fluidically connected to the entrance of the open capillary channel; and
        an open fillet cavity disposed in the body and fluidically connected to the exit of the open capillary channel;
        wherein at least one side of the open capillary channel is open for permitting viewing into, and;
        wherein at least one side of the open fillet cavity is open for permitting viewing into;

b) providing a liquid inside the source cavity; and c) using a high-speed imaging system with magnifying optics that faces an open side of the test specimen to observe and record the liquid flowing from the source cavity, along the open capillary channel driven by capillary action, and into the open fillet cavity.

19. The method of claim 18, wherein providing liquid inside the source cavity comprises melting a solder or braze wire or, preform pre-placed within the source cavity.

20. The method of claim 18, further comprising measuring the temperature of the test specimen with an embedded thermocouple; and using the measured temperature to control the heating of the test specimen.

21. The method of claim 18, further comprising:

capturing one or more of the recorded images from the high-speed video camera system; and using image analysis software to quantitatively extract a physical attribute of the behavior of the liquid from the captured images as a function of time;

wherein the physical attribute is selected from the group consisting of flow velocity, meniscus shape, fillet contact angles, liquid front profile, fillet shape, amount of overflow, temperature distribution, shrinkage, and residual strains.

* * * * *